(12) United States Patent
Levin et al.

(10) Patent No.: US 7,282,058 B2
(45) Date of Patent: Oct. 16, 2007

(54) SINGLE-USE LANCET DEVICE

(75) Inventors: Paul D. Levin, Santa Cruz, CA (US); Robby Jay Moore, Auburn, CA (US); David M. Levin, Santa Cruz, CA (US); Ted Ackley, Felton, CA (US); John D. Harding, Ben Lomond, CA (US)

(73) Assignee: Palco Labs, Inc., Scotts Valley, CA (US)

( * ) Notice: Subject to any disclaimer, the term of this patent is extended or adjusted under 35 U.S.C. 154(b) by 675 days.

(21) Appl. No.: 10/693,128

(22) Filed: Oct. 24, 2003

(65) Prior Publication Data
US 2004/0092997 A1  May 13, 2004

Related U.S. Application Data

(60) Provisional application No. 60/446,166, filed on Feb. 7, 2003, provisional application No. 60/422,630, filed on Oct. 29, 2002.

(51) Int. Cl.
*A61B 17/3209* (2006.01)
*A61B 5/151* (2006.01)

(52) U.S. Cl. ............ 606/181; 606/167; 604/157; 600/573

(58) Field of Classification Search ............... None
See application file for complete search history.

(56) References Cited

U.S. PATENT DOCUMENTS 4,527,561 A * 7/1985 Burns ............ 606/182
5,356,420 A   10/1994 Czernecki et al.
5,487,748 A   1/1996 Marshall et al.
6,168,606 B1  1/2001 Levin et al.
6,719,771 B1  4/2004 Crossman

FOREIGN PATENT DOCUMENTS

WO    WO 02/43591 A2    6/2002

* cited by examiner

*Primary Examiner*—Glenn K. Dawson
(74) *Attorney, Agent, or Firm*—Bruce H. Johnsonbaugh

(57) ABSTRACT

A single-use lancet device is provided for drawing capillary blood samples. The device includes a body having an upper portion and a lower portion and a trigger carried by the upper portion of the body. The trigger is movable between a first raised position wherein the device is cocked and a second depressed position wherein the device is fired. A needle assembly is provided which is movable between a cocked position and a striking position. A free-floating drive spring is provided for moving the needle assembly from its cocked position to its striking position. A bounceback spring is integrally molded with the needle assembly and includes a pair of generally V-shaped spring arms. A trigger bar has a first position wherein it holds the needle assembly in its cocked position, and the trigger bar has a second position wherein it allows the needle assembly to move to its striking position as the drive spring expands. The trigger carries a pair of guillotine-type blades which sever the trigger bar and thereby releases the needle assembly from its cocked position. Alternate trigger bars are provided which may be deformed rather than severed. The device is also capable of assembly by automatic equipment. The device is incapable of a second use because of the deformation or severing of the trigger bar.

33 Claims, 22 Drawing Sheets

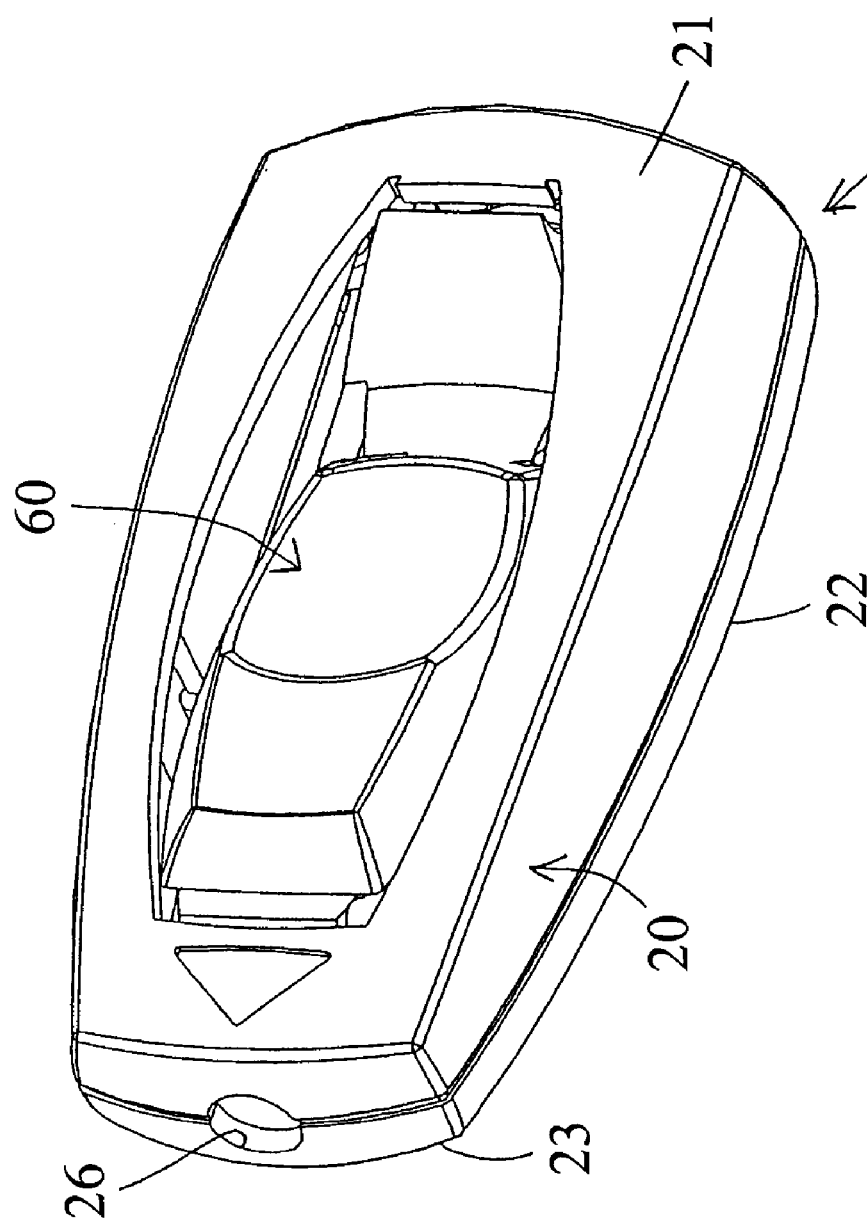

SINGLE-USE LANCET DEVICE

CROSS REFERENCE TO RELATED APPLICATIONS

This application claims the benefit of and priority from U.S. provisional applications Ser. No. 60/422,630 filed Oct. 29, 2002 and Ser. No. 60/446,166 filed Feb. 7, 2003.

BACKGROUND AND SUMMARY OF THE INVENTION

The present invention relates generally to single-use lancets for drawing capillary blood samples. In particular, the present invention provides a single-use lancet which for safety reasons is not capable of being used more than once. Reuse is prevented by a unique trigger mechanism which in the preferred embodiment is irrevocably broken upon firing. The dire consequences of reuse, such as the spread of hepatitis or HIV, are thereby avoided. Furthermore, the present invention is designed so that it may be assembled by automatic machinery. Automatic assembly reduces the cost of the device and assures the highest quality finished product.

Reliable attachment of the main spring to the rear end of the lancet and to the inner body of the device to cause "bounceback" after firing is a pervasive problem in prior art devices. If the spring becomes loose at either end, the lancet will fail to properly retract after firing. The present invention obviates this problem by using a "free floating" spring that does not require any attachments to either end of the lancet. Assembly is simplified and lancet bounceback after firing is reliably accomplished by utilizing plastic spring arms integrally molded into the lancet carrier.

A novel detachable tailpiece on the lancet carrier facilitates automatic or manual assembly. The tailpiece serves as a guide for dropping the spring onto the carrier and helps to stabilize the spring while it is being compressed. The method of spring assembly and cocking of the present invention reduces assembly cost and facilitates quality control.

The needle of single-use devices is driven into the patient's skin by a small spring, which is typically cocked by the technician just prior to use. The safety cap with its attachment keeps the end of the lancet sterile and, since it can be used as a kind of push rod, it is also employed by the user to cock the device. When pulled off, the needle is exposed and the device, having been cocked, is ready for use. Such a device is described in U.S. Pat. No. 5,487,748 to Marshall assigned to Owen Mumford.

One disadvantage of the Marshall device is the ease with which it can be recocked after use. The needle cap can simply be replaced over the end of the lancet and pushed inward to once again cock the spring of the lancet. A small metal rod such as a paperclip can also be used to recock the device described in '748. While such an action is unlikely by a professional blood drawer, it is nevertheless an undesirable feature of a lancet constructed in this fashion.

In an attempt to prevent recocking, another Owen Mumford patent W00243591 describes a single-use device in which the needle carrier has integrally formed spring arms extending rearwardly and alongside the lancet so that after firing, these arms will catch on abutments within the barrel of the device if recocking is attempted by the user. A disadvantage of this technique is that, if the lancet is pulled outward momentarily before being cocked by the user, the spring arms catch on the abutments and the device can therefore not be cocked.

Another method of preventing reuse of the device is described in U.S. Pat. No. 6,168,606 assigned to Palco Labs. In this device, a thin plastic fiber attached between the pull tab and the needle safety cap prevents any compressive force from being applied to the drive spring after firing which effectively prevents recocking of the device. The device must be cocked during manufacturing and is meant to be used after pulling off the finger tab which exposes the needle. A disadvantage of the '606 device is that a small bare area of the needle must remain exposed which could possibly result in airborne contamination since the device is not hermetically sealed.

BRIEF SUMMARY OF INVENTION

The configuration of the present invention has advantages not previously described in the prior art. The device is pre-cocked when it is manufactured and therefore makes cocking by the user unnecessary. In molding the bottom half of the case in the preferred embodiment, a small hole in the floor of the case allows a transverse trigger bar to be molded about 2 mm above the floor, in continuity with two vertical uprights. The intact trigger bar is positioned to bear against an abutment on the underside of the needle carrier. The bottom half of the device therefore provides both a channel for movement of the needle carrier and means to hold the carrier in place against the constant pressure from the compressed mainspring.

The top half of the device of the preferred embodiment of the invention carries the trigger button which can be moved downward about 3 mm when the concave button is pressed by the user. The underside of the button is provided with two vertical blades. When the trigger button is depressed, the blades descend and cut through the two end attachments of the trigger bar. The trigger bar rotates downward and forward, held by a small stem attached to the middle of the bar. The carrier is released and the cocked spring now drives the needle carrier forward causing a skin puncture. Spring arms integrally molded on the carrier in the preferred embodiment cause a bounceback of the lancet after the strike, so that it only momentarily protrudes from the aperture at the front of the device. The stem on the trigger bar presents it from becoming completely loose when the ends of the trigger bar are sheared from the vertical uprights. Since the trigger mechanism has been permanently broken by detachment of the trigger bar, the device cannot be recocked and a second use is impossible.

The present invention includes an advance in the manufacturing of single-use lancet devices relating to a novel method of cocking and assembly of the device which facilitates manufacturing the lancet either with automation or manually. In this technique to be described, a disposable tailpiece at the lower end of the lancet carrier allows the spring to be dropped onto the back end of the carrier and compressed before the needle carrier is placed inside the clam shell body.

The above-mentioned disposable tailpiece in the preferred embodiment is about 12 mm long, 4 mm wide and slightly less than 1 mm thick. During automated assembly, a coil spring of the proper diameter and length is loaded onto the tailpiece and then compressed by automatic machinery. While holding the spring compressed, the automation arm places the carrier into the proper location in the bottom half of the clamshell and the top half of the device is added, closing the device. The disposable portion of the carrier is then clipped off flush with the case. The assembly tool is now pulled out through a small horizontal slot in the back of the device. The technique speeds up assembly and avoids previously encountered problems in hand assembly such as escape of the compressed spring. The tailpiece also facilitates manual assembly, but automatic assembly is preferred.

OBJECTS OF THE INVENTION

A primary object of the invention is to provide a single-use lancet which cannot be reused.

A further object of the invention is to provide a single-use lancet which can be assembled by automatic equipment.

Another object of the invention is to provide a single-use lancet having a one-way trigger, wherein the trigger remains in its depressed firing position after the lancet has been used.

Another object of the invention is a single-use lancet having a free-floating mainspring for firing the device, and a bounceback spring integrally molded as a part of the movable needle assembly.

A further object of the invention is a single-use lancet which is pre-cocked during manufacture, and which does not have to be cocked by the user.

Yet another object of the invention is to provide a single-use lancet wherein the firing mechanism includes, in one embodiment, a pair of guillotine-type blades which partially sever a trigger bar detent, rendering the detent and the lancet device entirely incapable of reuse.

Other objects and advantages will become apparent from the following description and drawings.

BRIEF DESCRIPTION OF THE DRAWINGS

FIG. 3B is a perspective view of the device in its at rest position after it has been fired.

DETAILED DESCRIPTION OF THE DRAWINGS

The following description includes a description of the preferred embodiment shown in FIGS. 1-18. Alternate embodiments are thereafter described and shown in FIGS. 19-24.

Description of Preferred Embodiment

Figure 1:
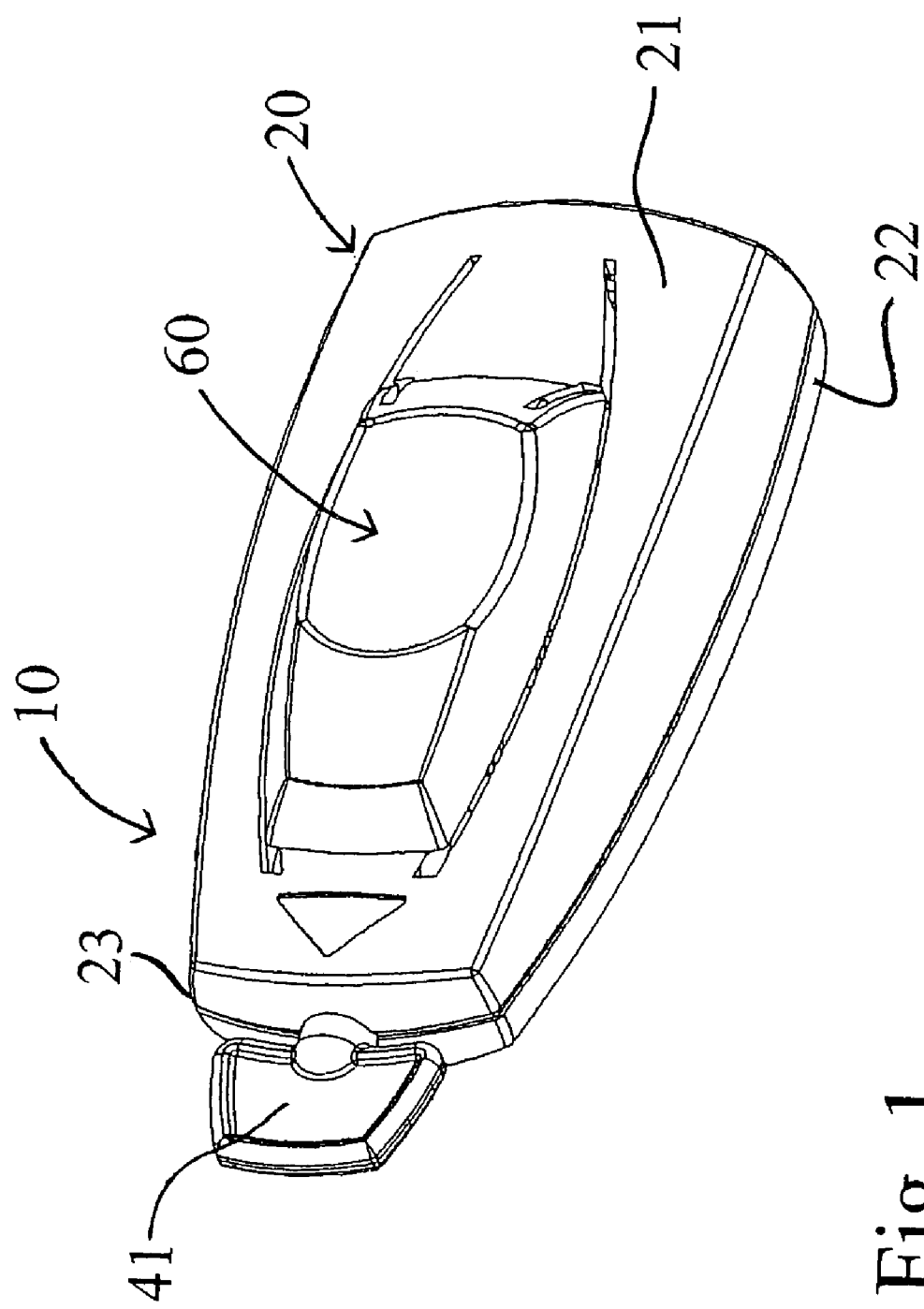
FIG. 1 is an overall perspective view of the device. The needle cover must be removed prior to use.

FIGS. 1-5 are perspective views of the preferred embodiment of the present invention. FIG. 1 illustrates the lancet device shown generally as 10 in its cocked position in which it is stored until ready for use. The body 20 of the device includes upper body portion 21 and lower body portion 22. Upper and lower body portions 21 and 22 may either be hingedly connected or may be separately formed and placed together in the position shown in FIG. 1 during the assembly process. A trigger shown generally as 60 in FIG. 1 is carried by upper body portion 21. Trigger 60 is shown in its first raised position in which the device is cocked. A plastic twist off safety cap 41 is shown extending outwardly from the distal end 23 of body 20. Cap 41 is integrally molded with the needle carrier assembly 40.

Figure 2:
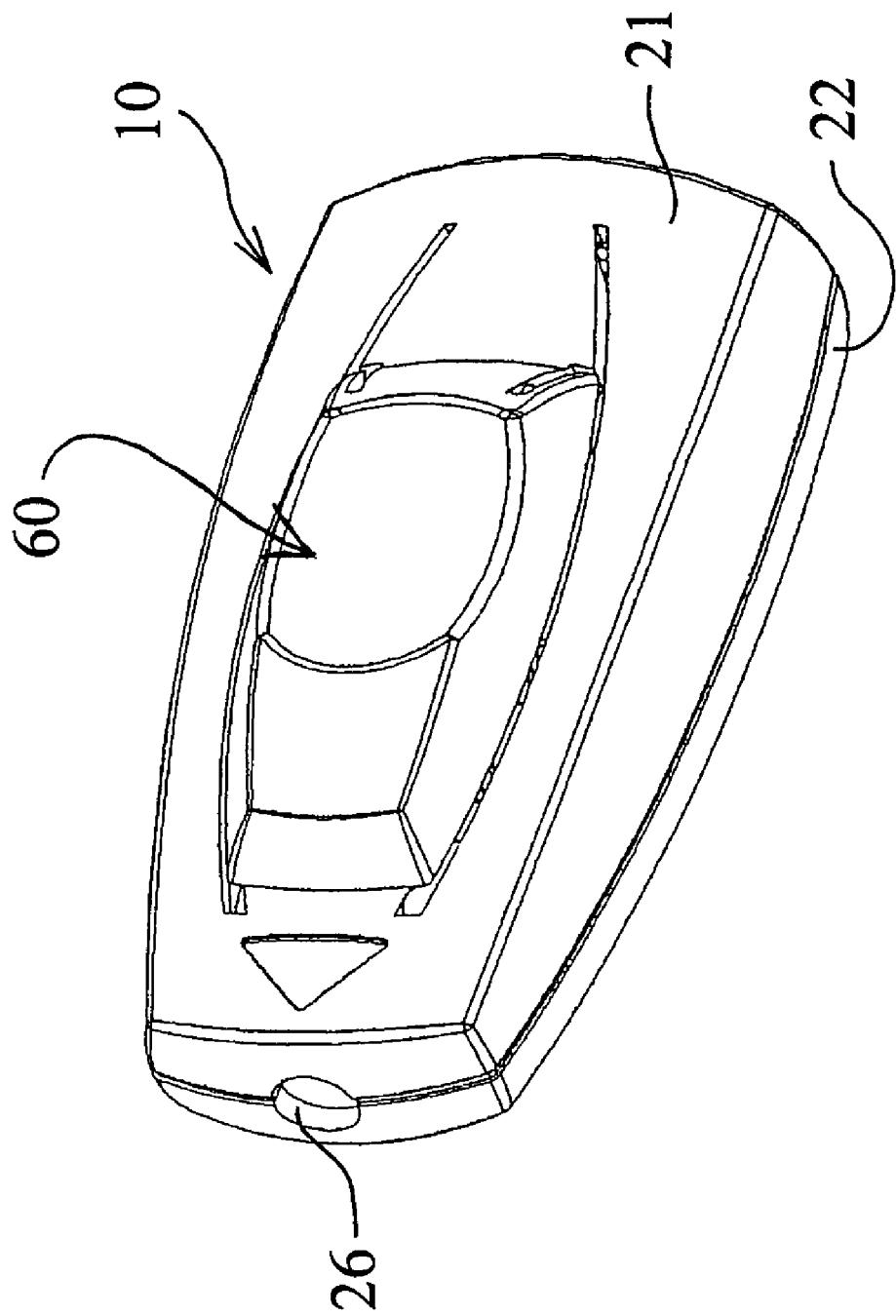
FIG. 2 is a perspective view of the device after the needle cover has been removed.

FIG. 2 illustrates the lancet device 10 after the safety cap 41 has been removed and the needle tip 45 (see FIG. 13) is exposed internally of the device and the device is ready to be fired.

Figure 3A:
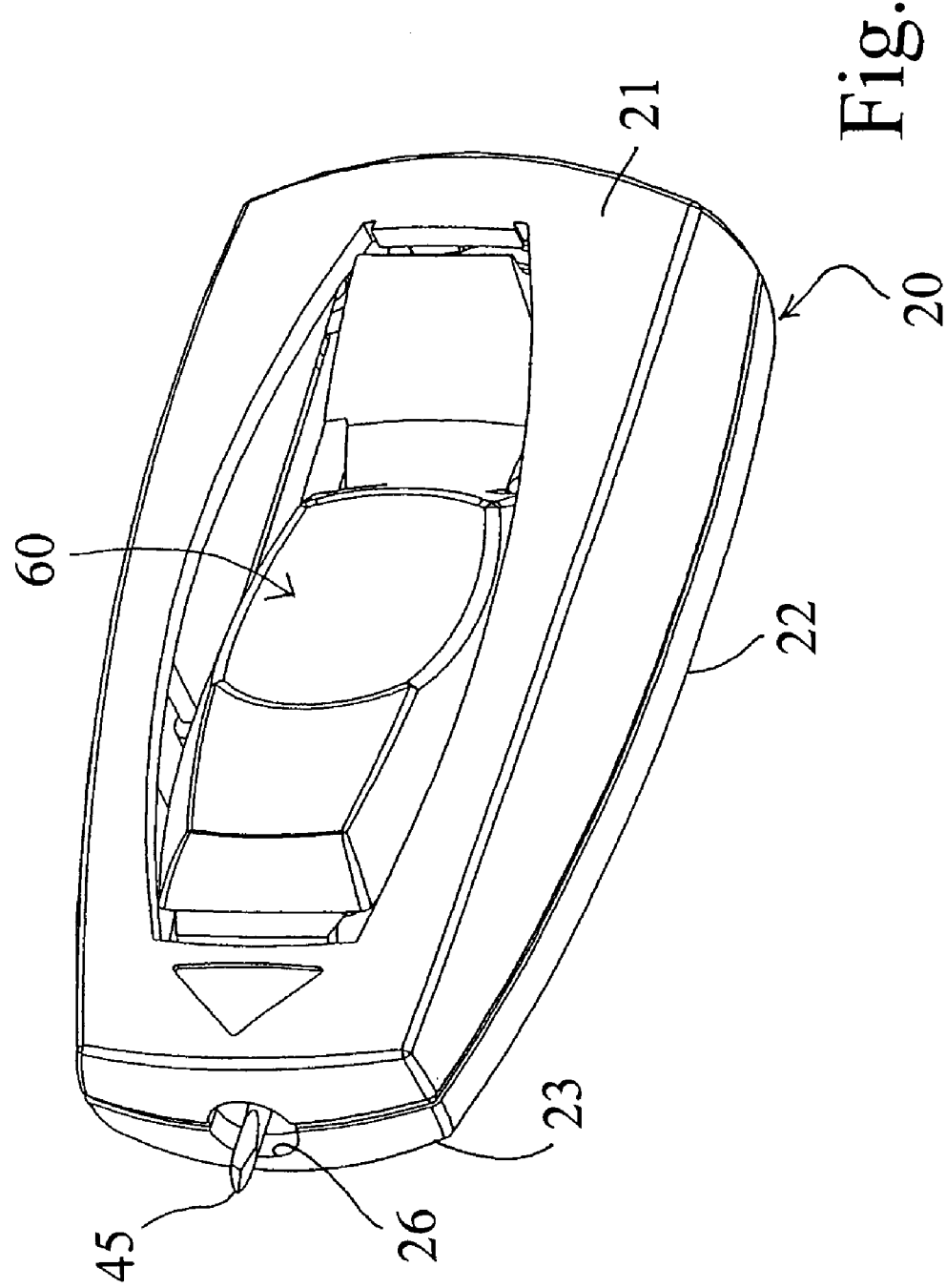
FIG. 3A is a perspective view of the lancet device at the moment of firing. The trigger button is depressed and the needle momentarily protrudes through the front aperture.

FIG. 3A illustrates the device 10 as the device is fired and as needle tip 45 momentarily protrudes through front or distal aperture 26 and reaches its striking position. Trigger 60 is shown in its second depressed position in which the device is fired.

FIG. 3B is a perspective view of the device 10 in its "at rest" position after it has been fired. The needle tip 45 is retracted through the front or distal aperture 26 formed at distal end 23 to a safe position within the periphery of body 20 (see FIG. 15). The trigger 60 is in its depressed position. The device cannot be used again.

Figure 4:
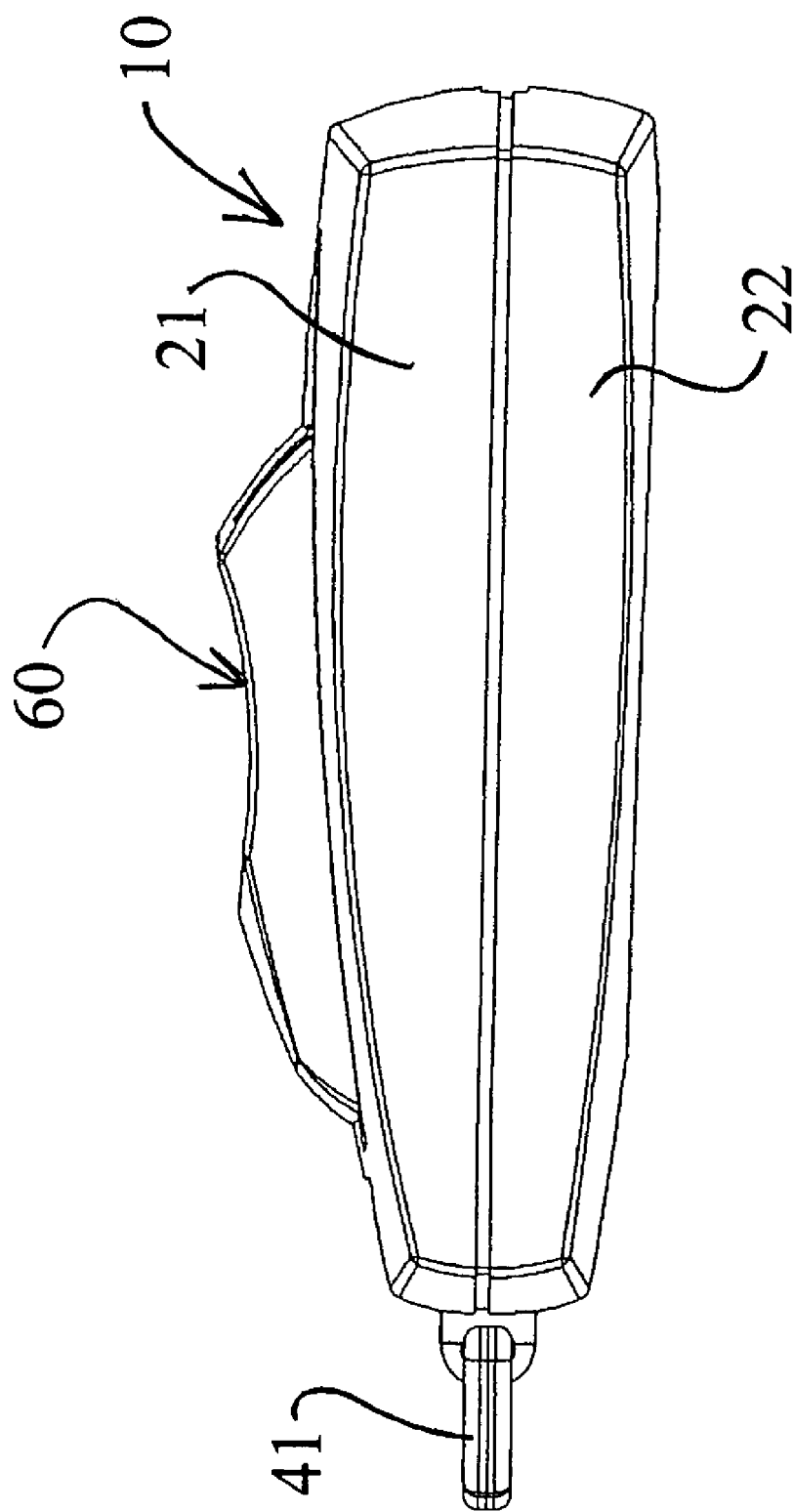
FIG. 4 is a side elevational view of the device prior to firing.

FIG. 4 is a side elevational view showing the device 10 as it is received by the user and in its cocked position.

Figure 5:
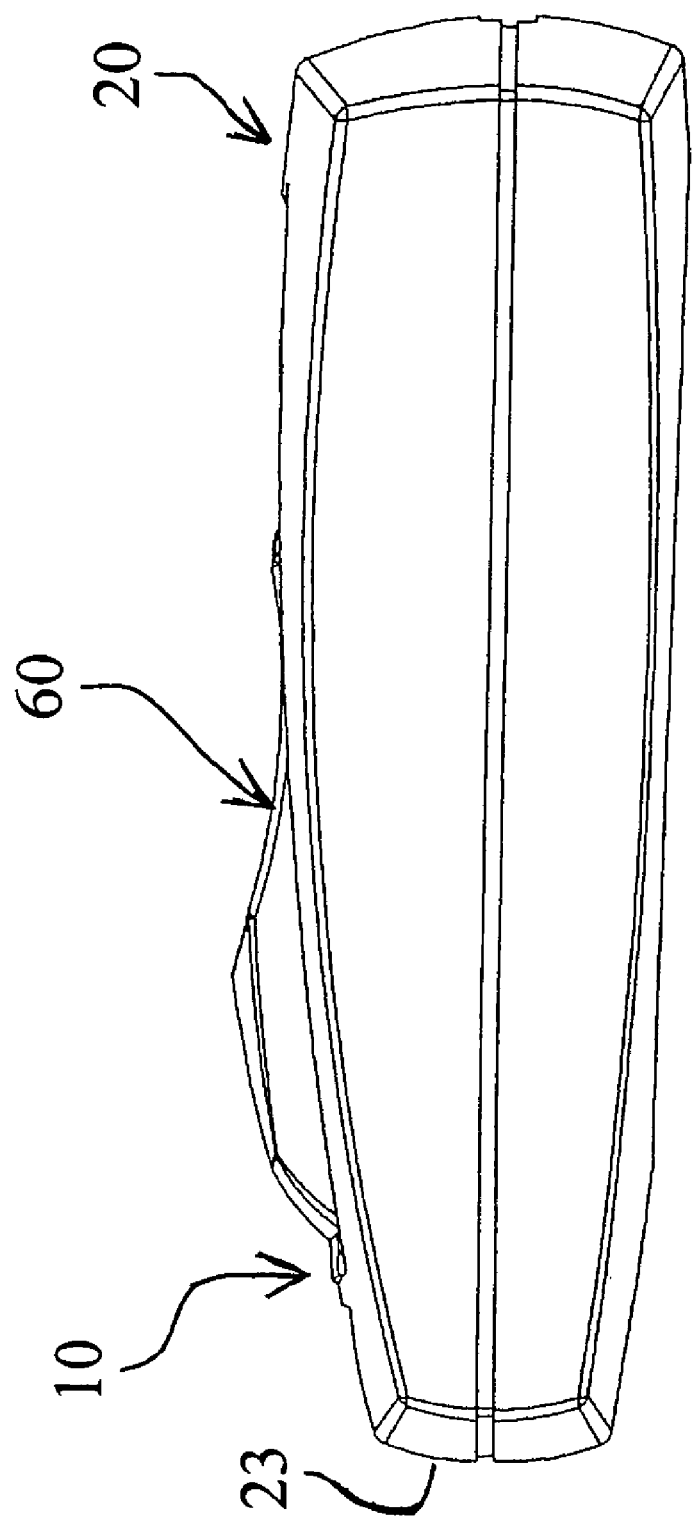
FIG. 5 is a side elevational view after firing showing the permanently depressed trigger button.

FIG. 5 is a side elevational view of the device 10 after the device has been fired and illustrating the second depressed position of trigger 60. Trigger 60 as shown in FIG. 5 is in its permanently depressed position because of the "over the center" design of the trigger assembly described in greater detail below. The needle tip 45 is not visible in FIG. 5 because it has been returned to a safe "at rest" position within the periphery of body 20 and wherein the needle tip is retracted inside distal end 23 of body 20 (see FIG. 15).

Figure 6:
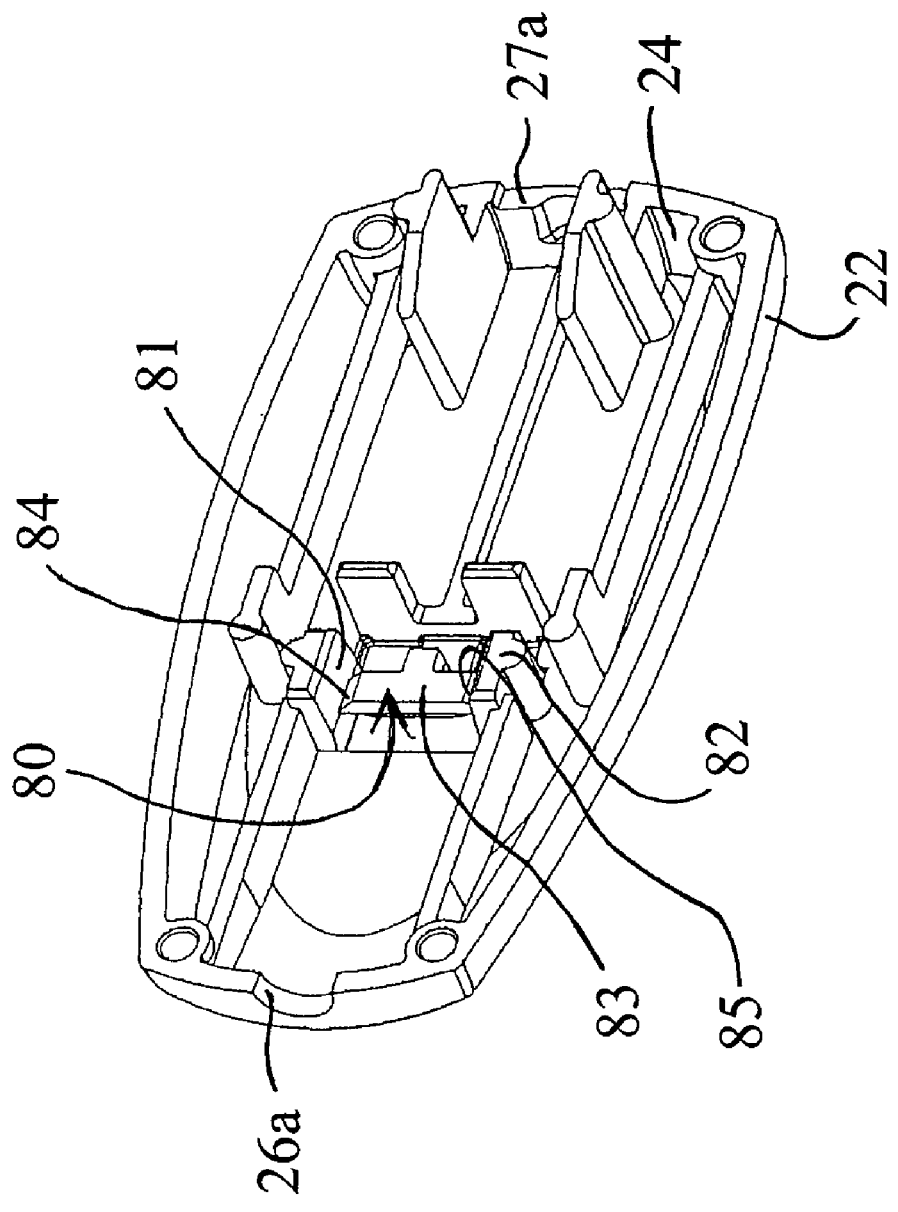
FIG. 6 is a perspective view of the bottom half of the lancet device showing the channel for the spring and needle carrier and the preferred embodiment of transverse trigger bar molded between two vertical uprights.

FIG. 6 is a perspective view illustrating the internal design of the bottom or lower portion 22 of body 20. The lower portion 22 includes numerous internal components that are integrally molded as a single piece 22 illustrated in FIG. 6. The lower half of distal aperture 26 is formed as recess 26a; the lower half of rectangular, proximal opening 27 (FIG. 16) is recess 27a, both formed in lower body portion 22. Trigger bar means 80 is integrally molded as a part of lower body portion 22 and extends between vertical uprights 81 and 82. Trigger bar means 80 includes vertical uprights 81,82 and transverse crossbar 83 having first and second tapered ends 84 and 85 of reduced cross section. As described in greater detail below, as the trigger 60 is actuated, the ends 84 and 85 of transverse crossbar or trigger bar 83 are severed from the vertical uprights 81 and 82, allowing the device to fire. Once the ends 84 and 85 have been severed, the trigger bar 83 is no longer capable of holding or retaining the needle assembly in its cocked position, thereby limiting the device to a single use.

Figure 7:
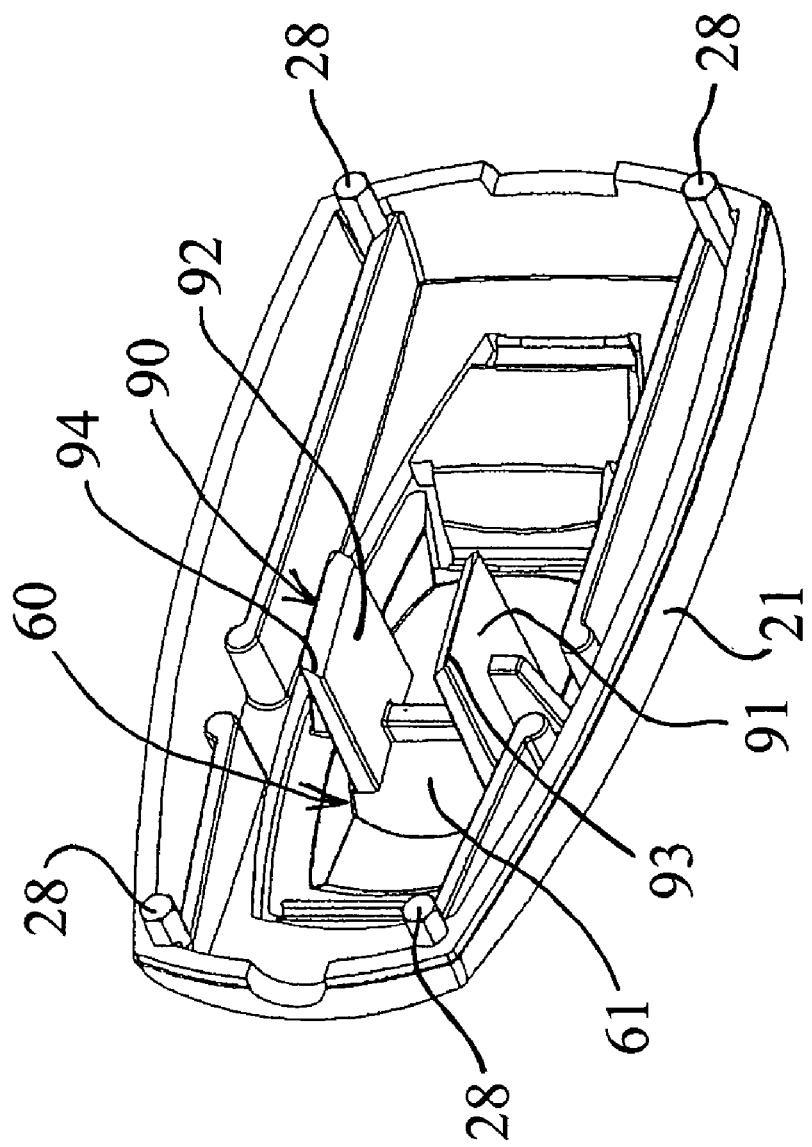
FIG. 7 is a perspective view of the top half of the device showing the underside of the trigger button which in this embodiment carries two vertical blades.

FIG. 7 is a perspective view of the inverted top portion 21 of body 20. The upper portion 21 illustrated in FIG. 7 is preferably a single molded piece containing numerous internal parts described below. The lower surface 61 of trigger 60 carries blade means shown generally as 90. In the preferred embodiment of the invention shown in FIG. 7, blade means 90 includes first and second guillotine-type blades 91 and 92 which extend downwardly from the lower surface 61 of trigger 60. Blades 91 and 92 preferably have beveled cutting tips 93 and 94, respectively, to shear transverse crossbar or trigger bar 83 (FIG. 6) as the device is fired.

Figure 8:
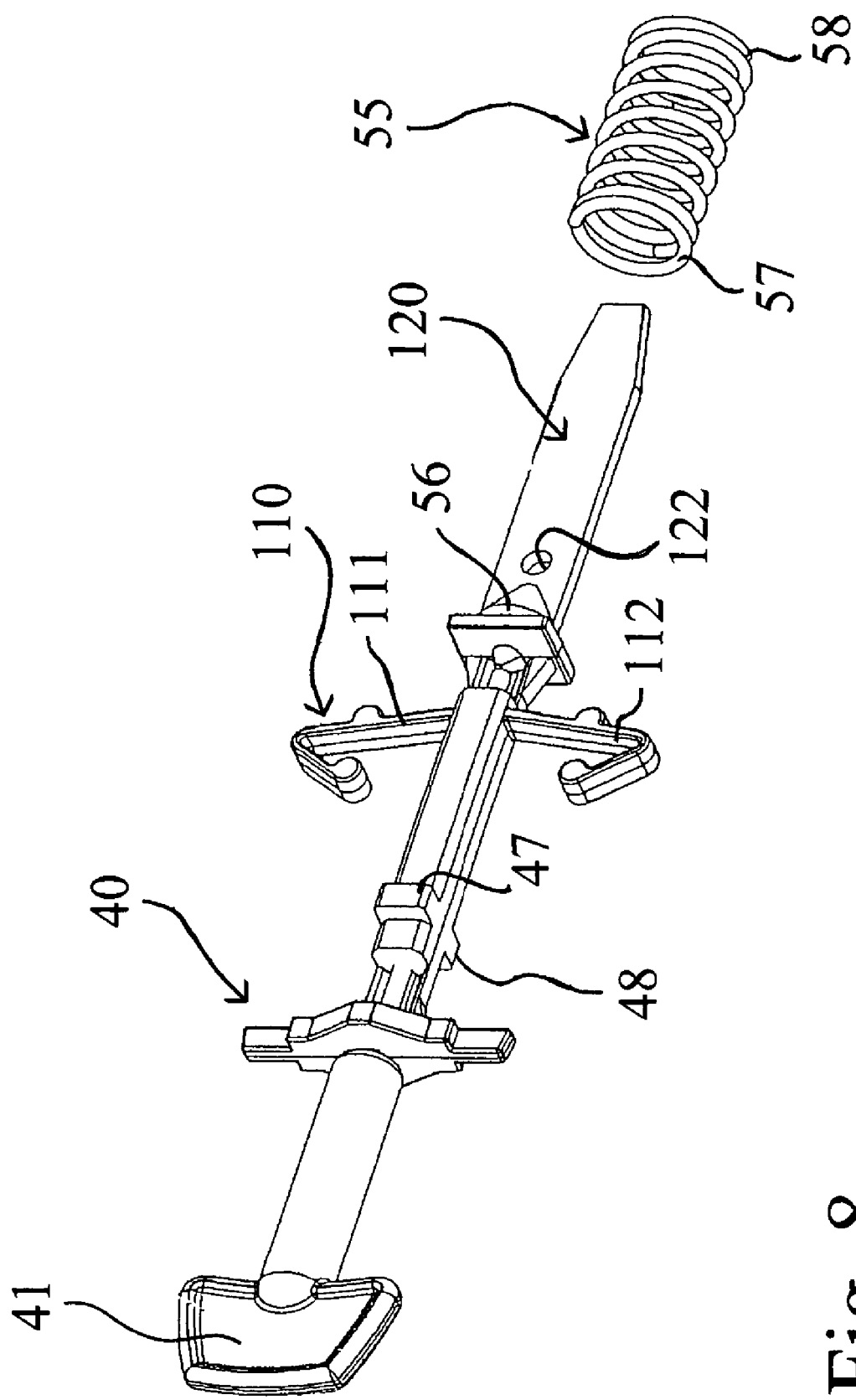
FIG. 8 is a perspective view of the needle carrier showing the tailpiece which guides placement of the drive spring. Also shown are the carrier bounce back arms, the abutments for the trigger bar and the needle cap.

FIG. 8 is a perspective view of needle carrier assembly or needle assembly shown generally as 40. Safety cap 41 covers the needle tip 45 (not visible in FIG. 8). Integrally formed as part of needle carrier assembly 40 is removable tailpiece 120, described in greater detail below, and a free floating helical drive spring 55. It is significant to note that the device of the present invention includes only a single, metallic and helical spring 55. The design utilizing only one spring which is free floating makes the device of the present invention capable of being assembled by automatic machinery, as described in detail below. The free floating mainspring or drive spring 55 serves to fire the device. A bounce back spring shown generally as 110 in FIG. 8 comprises a pair of generally V-shaped spring arms 111 and 112 which are integrally molded with plastic needle carrier assembly or needle assembly 40.

Abutments 47 and 48 are formed on the top and lower surfaces of needle carrier assembly 40. When the device is assembled, either abutment 47 or 48 will bear against transverse crossbar or trigger bar 83 and retain the needle carrier assembly in its cocked position in which mainspring or drive spring 55 is compressed. The purpose of having dual abutments 47 and 48 is to allow needle carrier assembly to be automatically assembled into the device with needle carrier assembly 40 capable of being installed with either side up.

Figure 9:
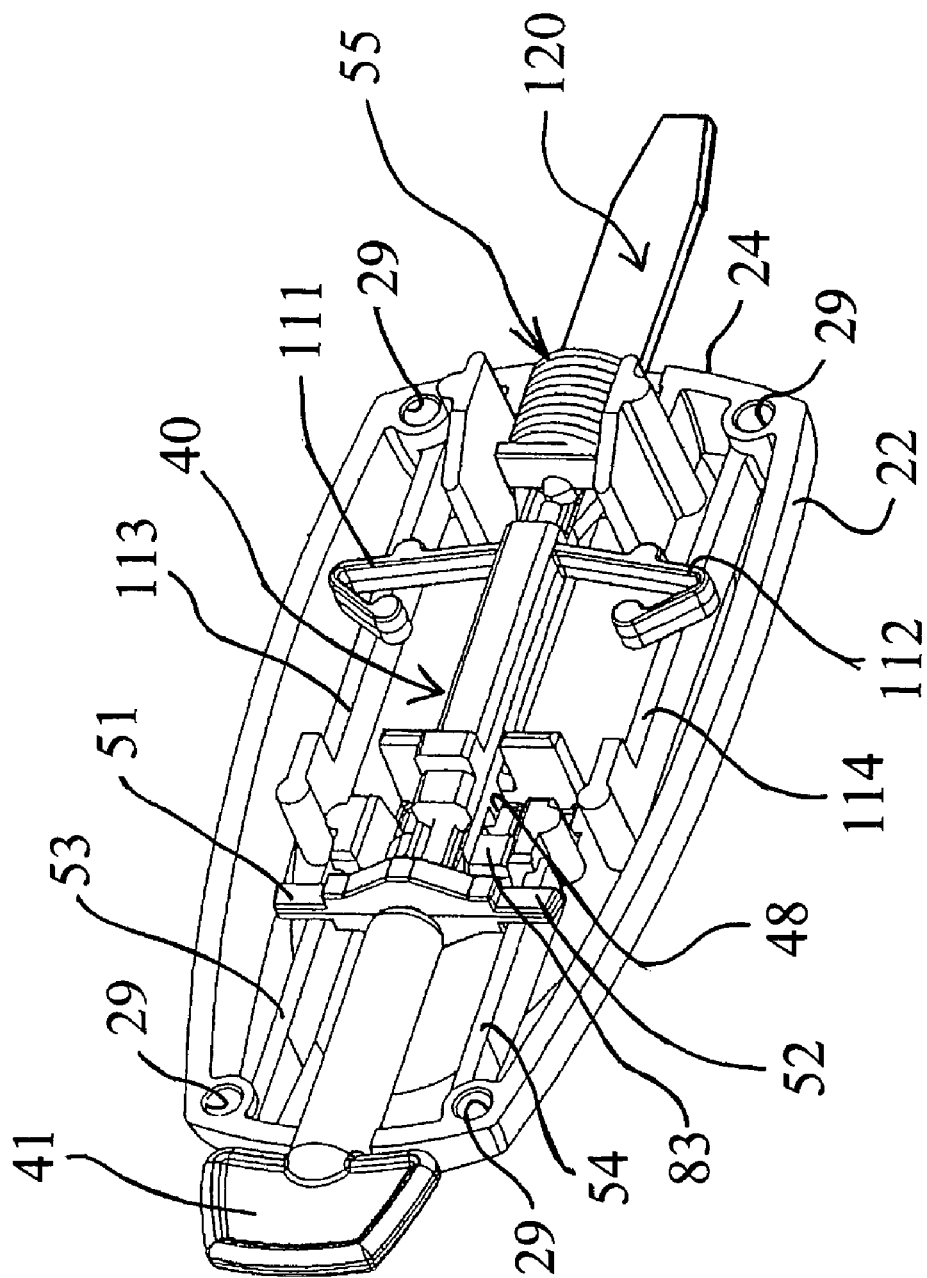
FIG. 9 shows the needle carrier of FIG. 8 inside the bottom half (FIG. 6) with the spring cocked. The top half of the device would ordinarily be present but has been removed for purposes of clarity.

FIG. 9 illustrates needle carrier assembly or needle assembly 40 as shown positioned in lower body portion 22. Upper body portion 21 has been deleted for the sake of clarity. As shown in FIG. 9, mainspring 55 has been slid onto removable tailpiece 120, fully compressed and seated against the proximal or back wall 24 of body 20. Abutment 48 is shown as it bears against transverse crossbar 83, holding needle carrier assembly 40 in its cocked position shown with mainspring 55 compressed. Spring arms 111 and 112 slide on horizontal rails 113 and 114 integrally molded into the lower body portion 22.

Needle carrier assembly 40 includes a pair of support arms 51 and 52 which slide on rails 53 and 54, respectively. Rails 53 and 54 are molded into lower body portion 22. The purpose of arms 51 and 52 is twofold. First, the arms 51 and 52 center and guide needle tip 45 (FIGS. 11-14) as the device is fired. Secondly, support arms 51 and 52 resist the twisting moment caused as the user rotates twist off cap 41 to expose the needle tip embedded therein.

Figure 10:
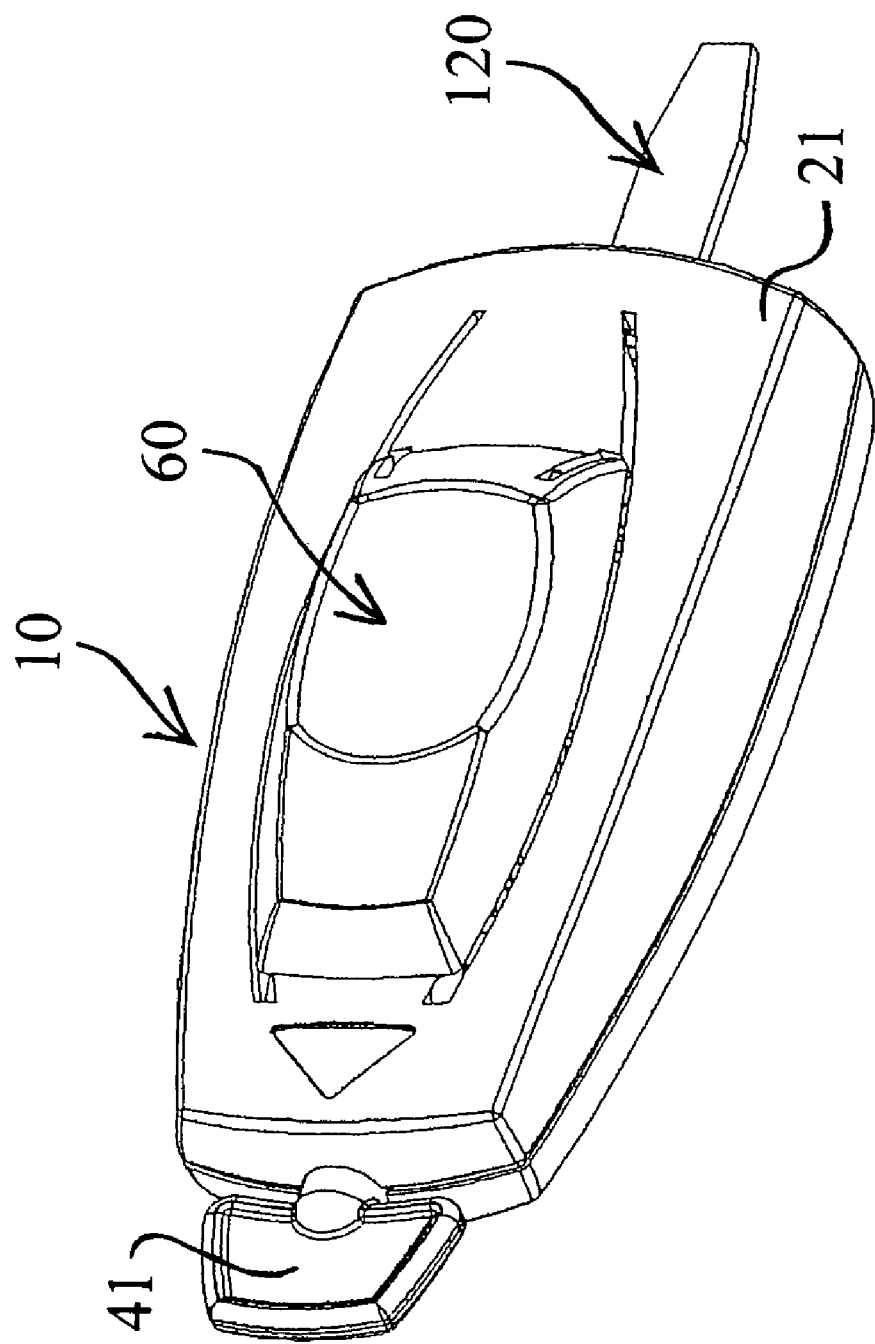
FIG. 10 is a perspective view of the assembled device prior to cutting off the tailpiece flush with the rear surface of the device.

FIG. 10 is a perspective view of the assembled device shown generally as 10 prior to the removable tailpiece 120 being severed.

Figure 11:
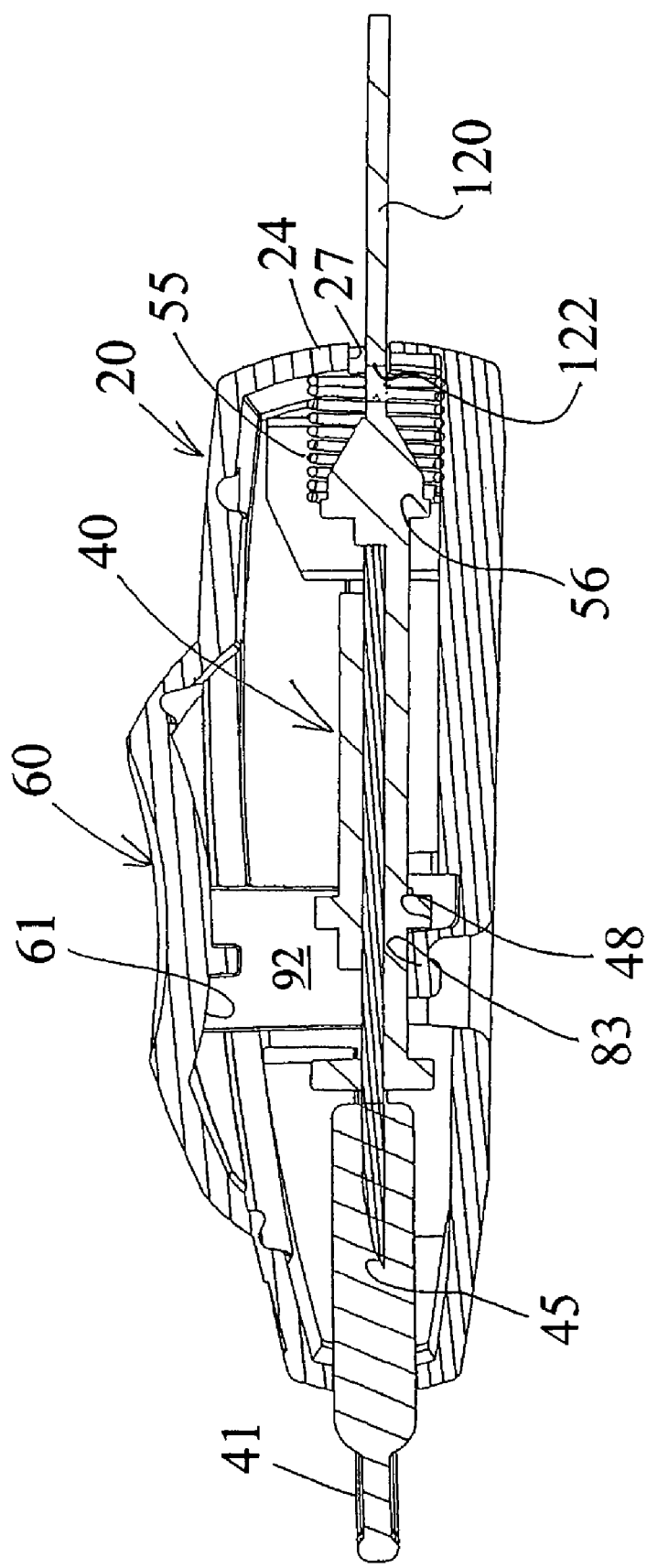
FIG. 11 is a sectional view of the device with the needle carrier in place and the drive spring cocked over the tailpiece.

FIG. 11 is a sectional view of the device illustrated in FIGS. 1-10 with the needle carrier 40 in place. Trigger 60 is in its first raised and cocked position. Blade 92 is carried by the underside 61 of trigger 60. Needle tip 45 is shown embedded within twist off safety cap 41. Abutment 48 is shown bearing against transverse trigger bar 83. Mainspring 55 is in its compressed position. It is significant to note that mainspring or drive spring 55 is "free floating" in the sense that it simply bears against the rear or proximal wall 24 of body 20 and against spring seat 56 formed on needle carrier assembly 40. Removable tailpiece 120 is shown in FIG. 11 as it extends through opening 27 formed in the rear or proximal wall 24 of body 20.

Figure 12:
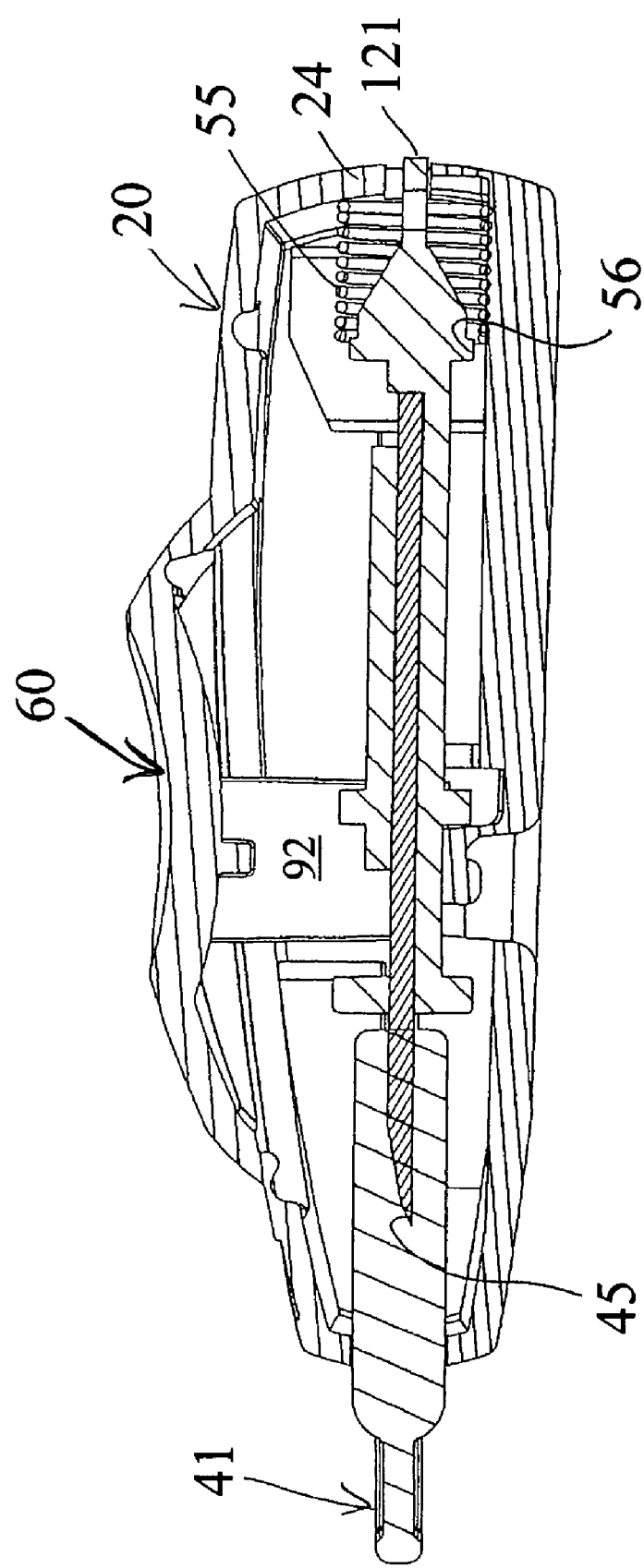
FIG. 12 is a sectional view after cutting off the tailpiece flush with the surface of the device.

FIG. 12 is a sectional view of the device illustrated in FIGS. 1-11 wherein removable tailpiece 120 (FIG. 11) has been cut off flush with rear or proximal wall 24 of body 20, leaving surface 121 flush with proximal or back wall 24.

Figure 13:
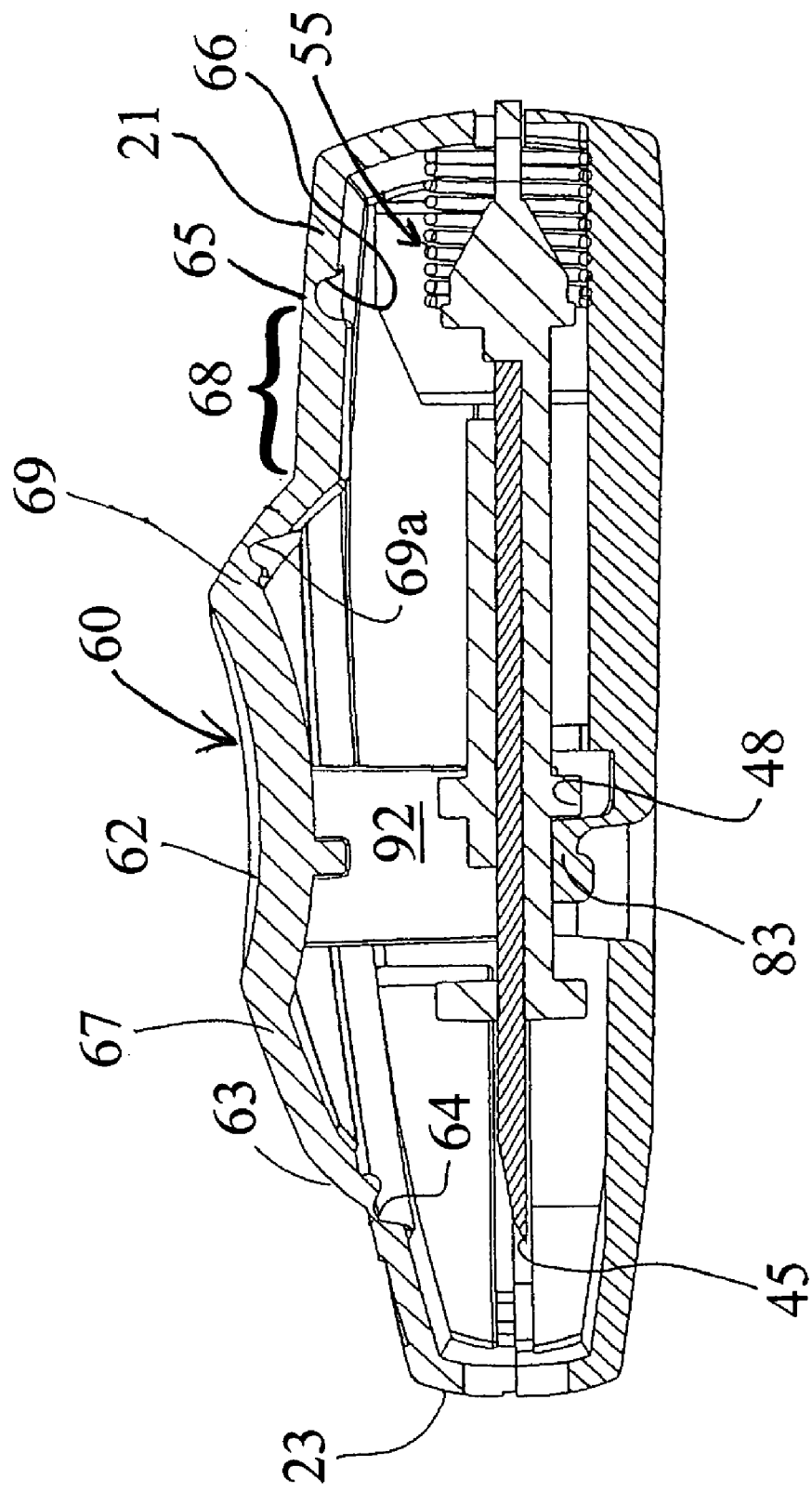
FIG. 13 is a sectional view after removal of the needle cover.

FIG. 13 is a sectional view after the twist off safety cap 41 (FIG. 12) has been removed, exposing needle tip 45. As shown in FIG. 13, the device is now ready to be fired.

Figure 14:
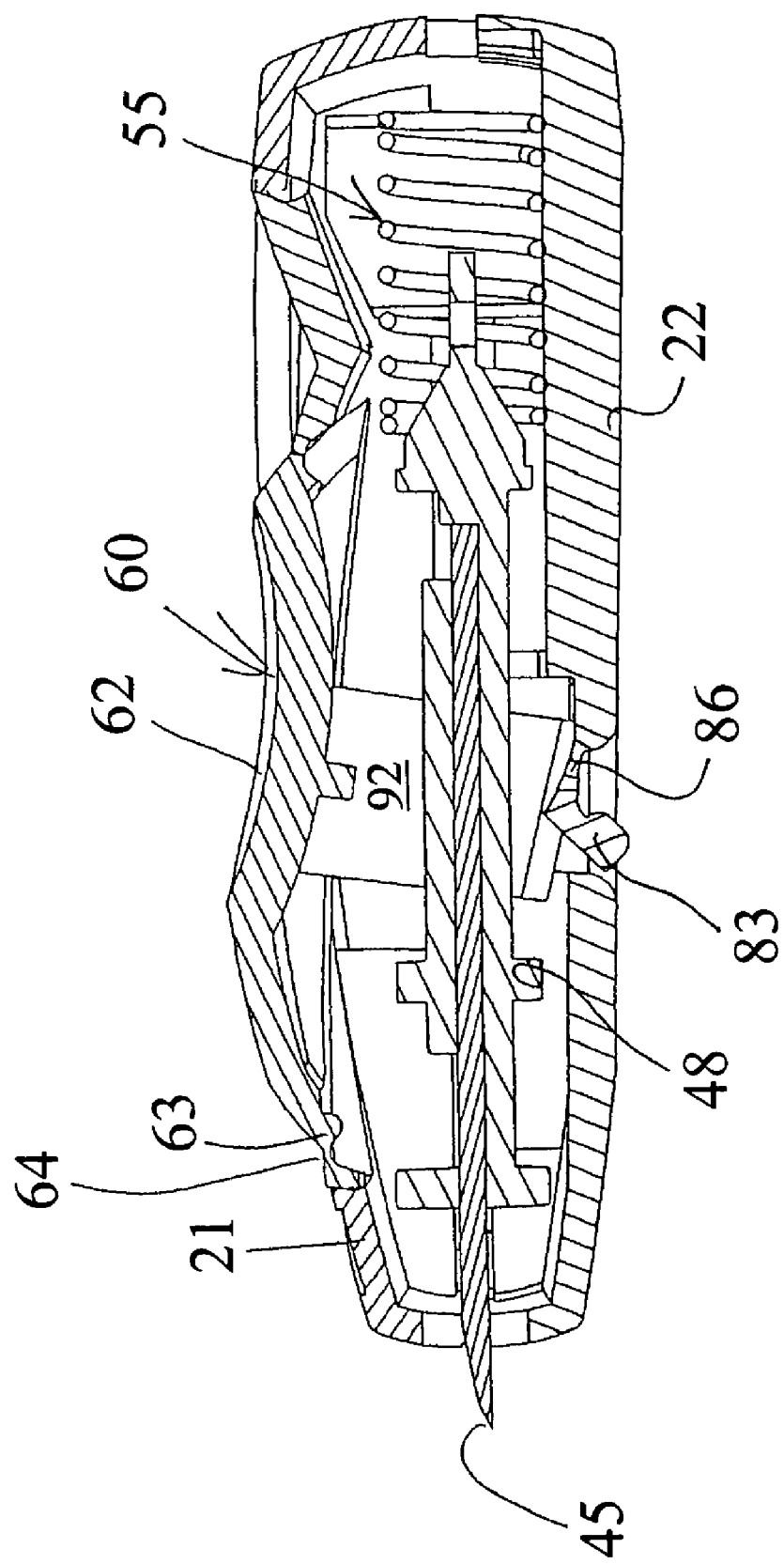
FIG. 14 is a sectional view showing the trigger button depressed and the lancet momentarily protruding from the front or distal aperture.

FIG. 14 is a sectional view on the same line as the sectional views of FIGS. 11-13. In FIG. 14, the trigger 60 has been depressed and is shown in its second depressed position in which the device is fired. Blade 92 has descended and severed the tapered ends 84 and 85 of transverse trigger bar 83, as shown best in FIGS. 17 and 18. As transverse trigger bar 83 is partially severed by blades 91 and 92, lug 48 is free to move forwardly as drive spring 55 expands. Needle tip 45 and needle assembly 40 are shown in FIG. 14 in their striking position in which needle tip 45 pierces the skin of the user to allow a blood sample to be obtained.

Transverse crossbar or trigger bar 83 is connected to the lower portion 22 of body 20 by support stem 86. Support stem 86 is bendable downwardly as the device is fired and prevents the partially severed transverse trigger bar 83 from falling out of the device.

As shown best in FIGS. 13 and 14, trigger 60 has a concave surface 62 adapted to receive a user's fingertip. Trigger 60 has a distal end 63 pivotally connected to the upper portion 21 of body 20. The pivotal connection is a reduced thickness portion 64 which acts as a pivot for the distal end of one-way trigger 60. The proximal end 65 of trigger 60 comprises a reduced thickness 66 of upper body portion 21. Trigger 60 includes a first segment 67 forming the distal end of trigger 60 including the concave surface 62 adapted to receive a user's fingertip. A second segment 68 forms the proximal end of the trigger 60. A third segment 69 is an intermediate and inclined segment that connects segments 67 and 68. A third pivot point 69a is formed as a reduced thickness in third segment 69. The use of these three segments creates an over-the-center motion of the trigger when depressed and creates an instability of the trigger at intermediate positions between the cocked position shown in FIG. 13 and the firing position shown in FIG. 14. The over-the-center motion holds the trigger down after the device is fired. One-way trigger 60 has a running length, measured along the inclined surface of segment 69 and the surfaces of first and second segments 67,68 which exceeds the "straight line" distance between the distal and proximal ends 63 and 65.

Figure 15:
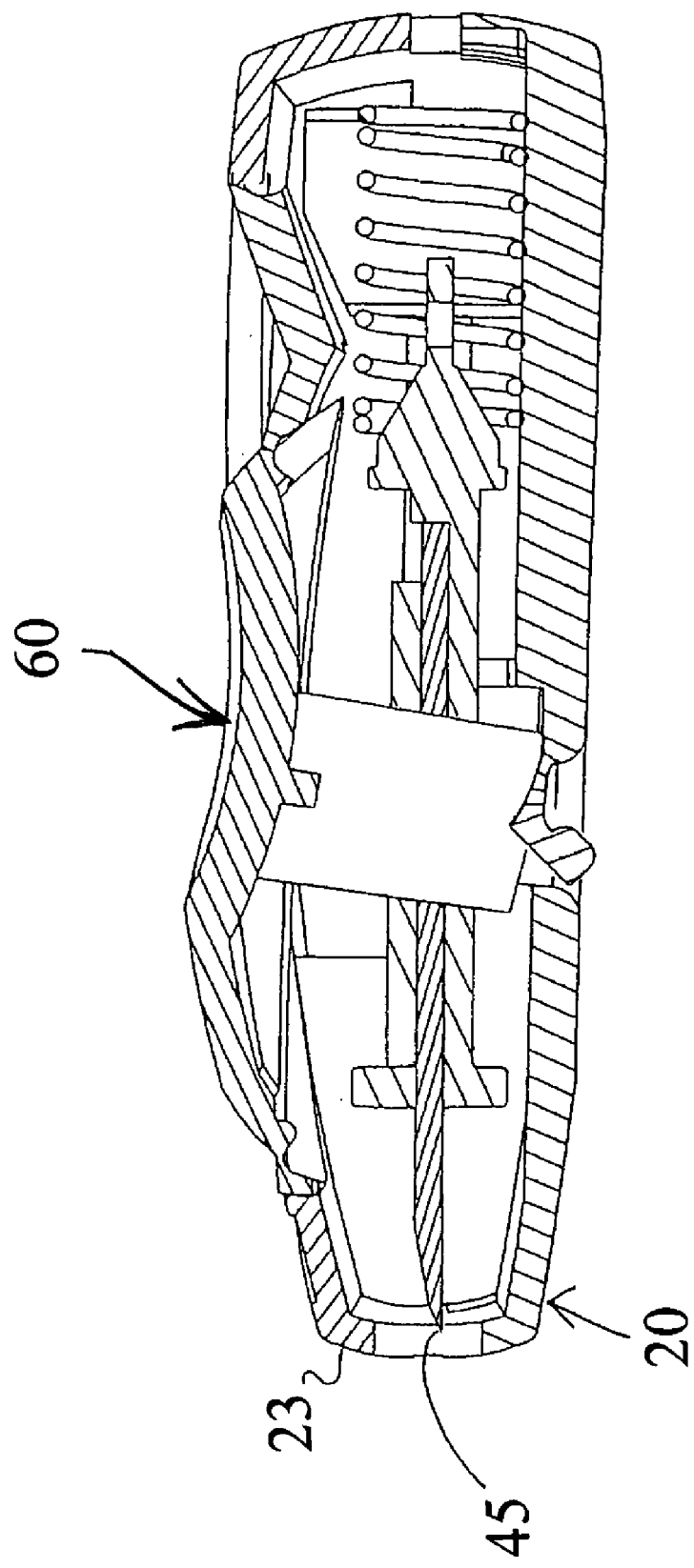
FIG. 15 shows the lancet retracted back inside the device after the needle strike.

FIG. 15 is a sectional view on the same line as FIGS. 11-14 shortly after the needle tip 45 has made its strike and has been retracted by bounceback spring 110 (see FIGS. 8 and 9) to an "at rest" position wherein needle tip 45 is withdrawn back into body 20 and needle tip 45 is inwardly of the distal end 23 of body 20; the device cannot be used again.

Figure 16:
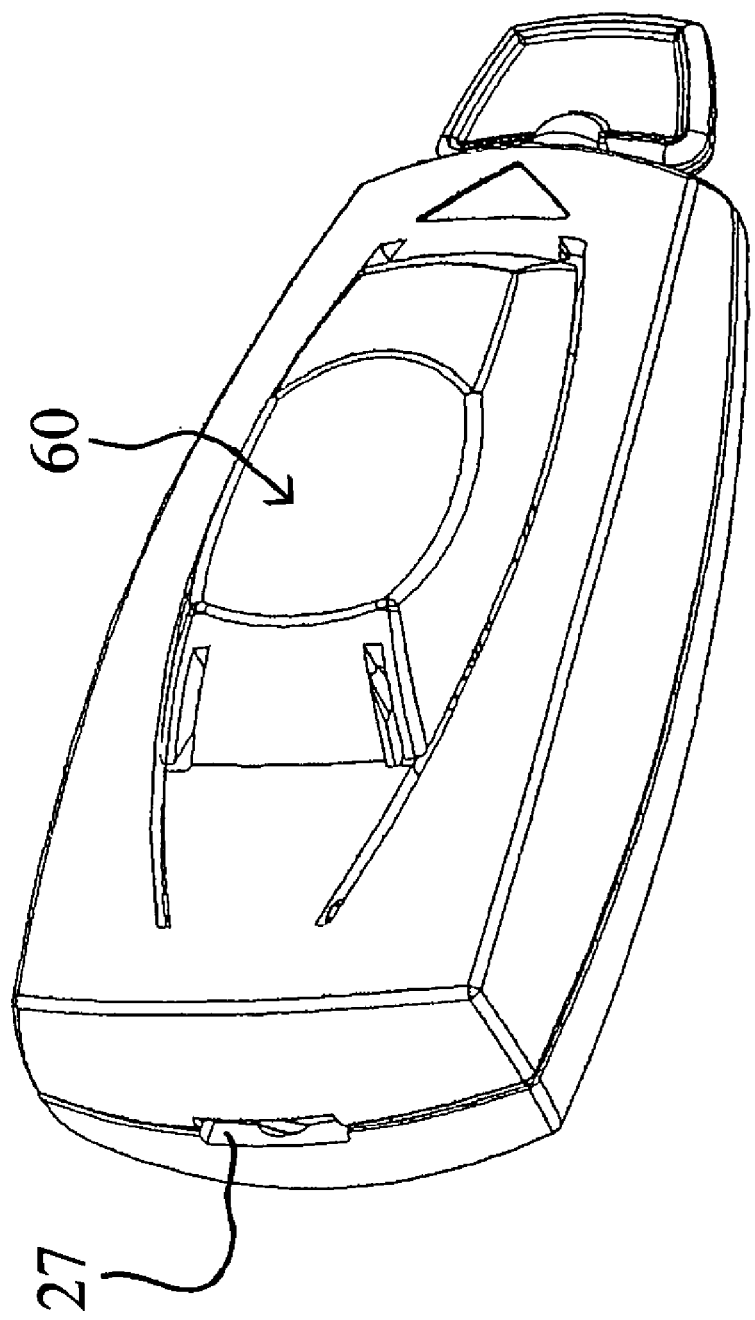
FIG. 16 shows the small slot in the back of the device through which the cocking tool (not shown) cocks the drive spring.

FIG. 16 shows the rear of the device and rectangular opening 27.

Figure 17:
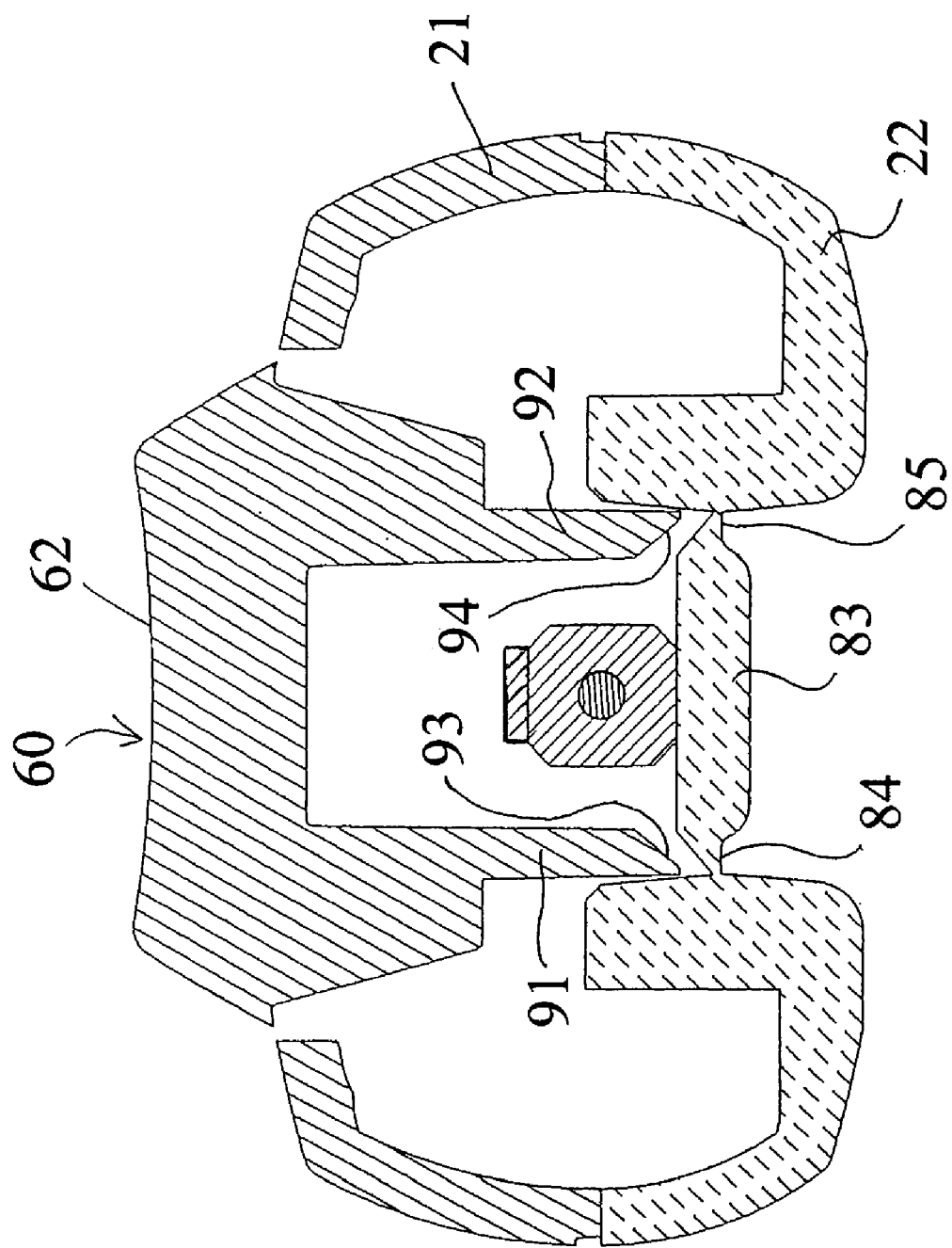
FIG. 17 is a sectional view of a portion of the device showing the position of the trigger bar prior to firing.
Figure 18:
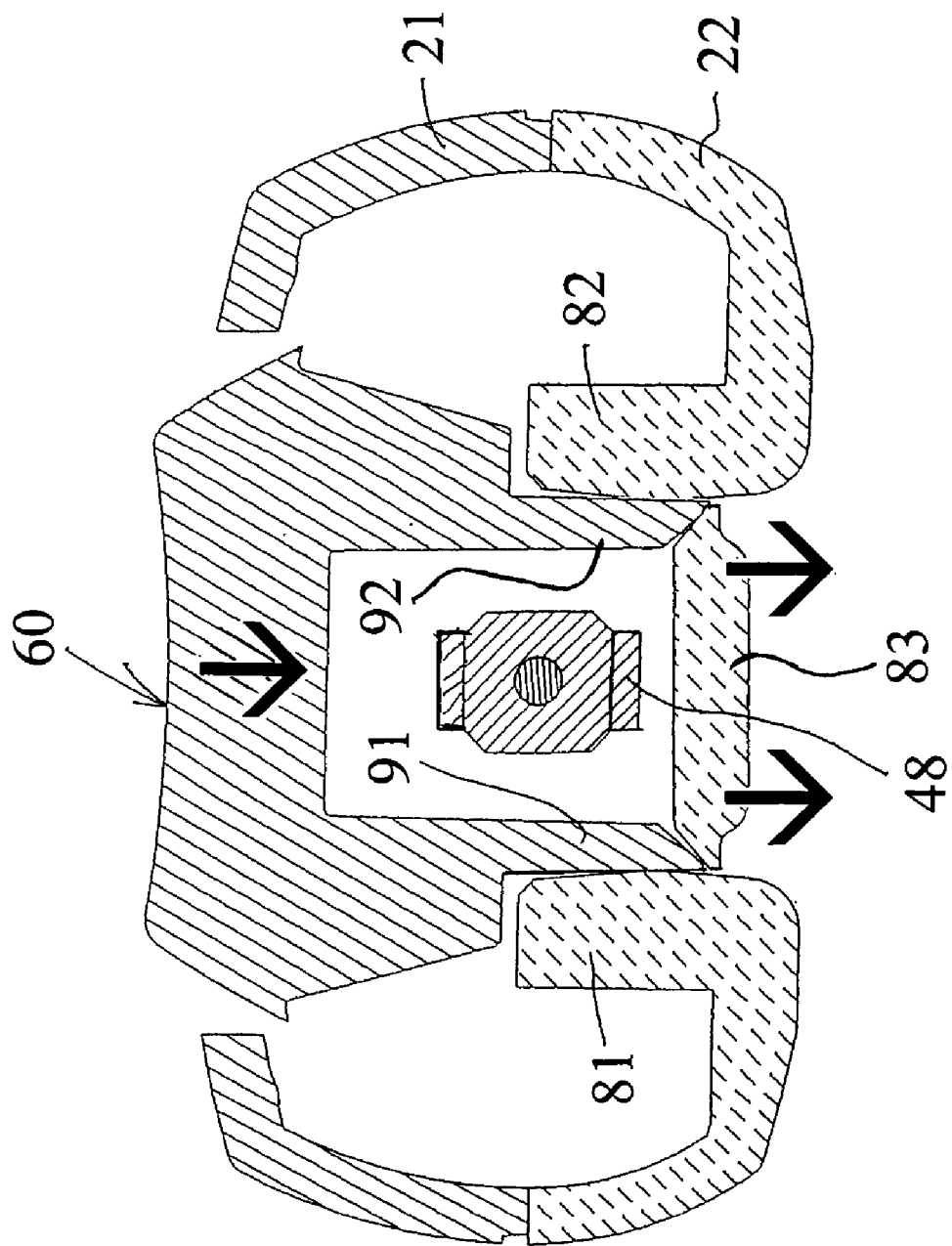
FIG. 18 is a sectional view of a portion of the device after firing showing the trigger bar severed and unable to hold the needle carrier against the force of the spring.

FIGS. 17 and 18 are schematic representations illustrating the action of guillotine blades 91 and 92 (see FIGS. 7,13 and 14). As shown in FIG. 17, the device is in its cocked position. Trigger 60 is in its first raised position and the beveled tips 93 and 94 of guillotine blades 91 and 92 are positioned above the reduced thickness ends 84 and 85 of transverse trigger bar 83. Trigger bar means 80 is shown in its first position wherein it holds the needle assembly in its cocked position.

As shown in FIG. 18, as trigger 60 is moved to its second depressed position, guillotine blades 91 and 92 move downwardly and sever transverse crossbar or trigger bar 83 from vertical uprights 81 and 82. In the position shown in FIG. 18, transverse crossbar or trigger bar 83 has been partially severed from the lower portion 22 of the body 20. As noted above, a vertical support stem 86 (not shown in FIG. 18 for clarity) extends upwardly from lower body portion 20 to the center portion of transverse trigger bar 83 and keeps the severed trigger bar 83 from falling outwardly of the device. When the transverse crossbar or trigger bar is severed and moves to its second position, as shown in FIG. 18, lug 48 and needle assembly 40 are released and move forwardly to the striking position and the device is fired as the mainspring 55 expands.

Free-Floating Mainspring

The preferred embodiment of the present invention includes a free-floating mainspring 55 (FIG. 8), wherein neither end of the spring must be captured by or connected to the housing or the needle carrier. Prior art devices typically require engagement of the mainspring with the housing and/or needle carrier to cause a "bounceback" of the needle tip after firing. For example, the Marshall U.S. Pat. No. 5,487,748 and International Publication No. WO 98/58584 require such engagement. If those prior art devices are not assembled with proper engagement of the mainspring, the lancet will not retract after firing. Engagement of the mainspring adds significant cost to the assembly process. Some prior art devices use a molded, plastic mainspring which is formed integrally with the housing. Such integrally formed mainsprings limit the spring constants utilized for the mainspring.

The present invention achieves the desired bounceback by providing bounceback spring arms 111 and 112 integrally molded as part of needle carrier assembly 40. Spring arms 111 and 112 comprise bounceback spring means and therefore obviate the need for a mainspring which is engaged with the housing and/or needle carrier to cause bounceback.

The combination of a free-floating mainspring with integrally molded bounceback arms is advantageous for several reasons. First, the assembly process is easier to automate, increasing quality and decreasing cost. Secondly, a wider range of spring constants and spring designs may be used for the mainspring and bounceback arms.

Assembly of the Device

The design of the single-use lancet of the present invention lends itself to either automatic or manual assembly. FIGS. 6-13 illustrate the primary steps of the assembly operation. Automatic assembly is described below. The identical steps can be performed manually, although the preferred method includes the use of automatic equipment. In the first step of the operation, as shown in FIG. 6, the lower body portion 22 is supported and is ready to receive needle carrier assembly 40. In the next step of the operation, mainspring 55 is automatically loaded onto tailpiece 120. Next, mainspring 55 is automatically compressed against spring seat 56 and held in its compressed position (FIGS. 8 and 9). As shown best in FIG. 9, the needle assembly 40 with mainspring 55 temporarily held in its cocked position on tailpiece 120 is automatically loaded into lower body portion 22. In this position, the distal end 57 of mainspring 55 is seated against seat 56. The proximal end 58 of mainspring 55 is seated temporarily against a compression tool (not shown).

As shown best in FIG. 10, the next step in the assembly process is to automatically close the device by attaching upper body portion 21 to lower body portion 22. As shown best in FIG. 7, upper body portion in the preferred embodiment has pins 28 which are inserted into holes 29 formed in lower body portion 22. In the preferred embodiment, a frictional fit is formed between pins 28 and holes 29. After the single-use lancet 10 has been closed as illustrated in FIG. 10, the automatic compression tool (not shown for clarity) is withdrawn through rectangular opening 27.

Tailpiece 120 has a hole 122 formed in it, which hole engages an automatic compression tool (not shown). As shown best in FIG. 11, hole 122 is positioned adjacent the back or proximal wall 24 of the device. The compression tool is removed through rectangular opening 27 (FIGS. 11 and 16). Spring 55 now seats directly against the back wall 24. Spring 55 is "free-floating" in that neither the distal end 57 nor the proximal end 58 need engage the needle carrier or the housing to create a "bounceback" of the needle after firing.

After the compression tool is removed, that portion of the tailpiece 120 that extends outwardly of rear wall 24 is severed flush with rear wall 24 as shown best in FIG. 12. The device is therefore cocked, as shown in FIG. 12, since mainspring 55 is compressed and in its cocked position, the device is ready to be shipped.

Description of Alternate Embodiments

It is significant to note that the preferred embodiment disclosed herein utilizes a one-way trigger having an "over the center" actuating mechanism. Alternate trigger designs may be utilized with the invention, including trigger designs as illustrated in U.S. Pat. No. 6,168,606, incorporated herein by reference. Other trigger designs may be utilized, provided that the trigger is able to carry a blade which is capable of severing or otherwise deforming or irreparably breaking the trigger bar means which retains the needle assembly 40 in its cocked position.

Alternate forms of the trigger bar means can also be utilized in the invention. Although the preferred embodiment utilizes a transverse bar which is severed as described above, it is also possible to deform a transverse trigger bar. For example, a compressible trigger bar could be utilized which is compressed against the bottom of lower body portion 22. As the trigger is depressed, the compressible trigger bar would be plastically deformed and would be incapable of a second use. As used herein and in the claims, the term "deform" is used to include severing, irreparably breaking and "plastic" deformation wherein the material is permanently deformed beyond its elastic limit and is incapable of returning to its original position. Other alternate trigger bar means could be used provided that the trigger bar means is sufficiently deformed, severed or broken by the action of the blade means such that the trigger bar means is incapable of returning to its starting position and retaining the needle assembly in its cocked position against the compressed mainspring.

FIGS. 19-24 illustrate alternate trigger bar means.

Figure 19:
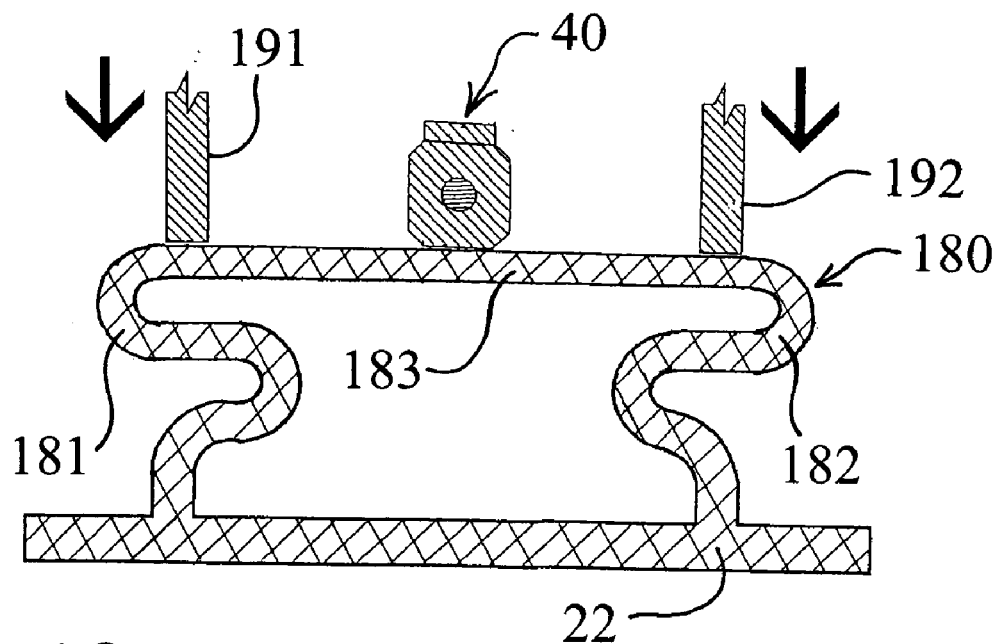
FIG. 19 is a schematic representation of an alternate compressible trigger bar.

FIG. 19 illustrates a compressible trigger bar means 180. It includes a pair of generally S-shaped arms 181 and 182 and top rail 183 integrally molded into the lower body portion 22. Top rail 183 contacts abutment 48 (not visible in FIG. 19). The arms 181 and 182 have a sufficient width to retain needle carrier assembly 40 in its cocked position illustrated in FIG. 19. The width of arms 181 and 182 extends perpendicularly out of the plane of the drawing of FIG. 19. The thickness of arms 181 and 182 is sufficiently thin to allow the trigger bar means 180 to be compressed as the blade arms 191 and 192 are pressed downwardly in the direction of the arrows by depressing the trigger button. FIG. 19 illustrates trigger bar means 180 in its first extended position wherein the device is cocked.

Figure 20:
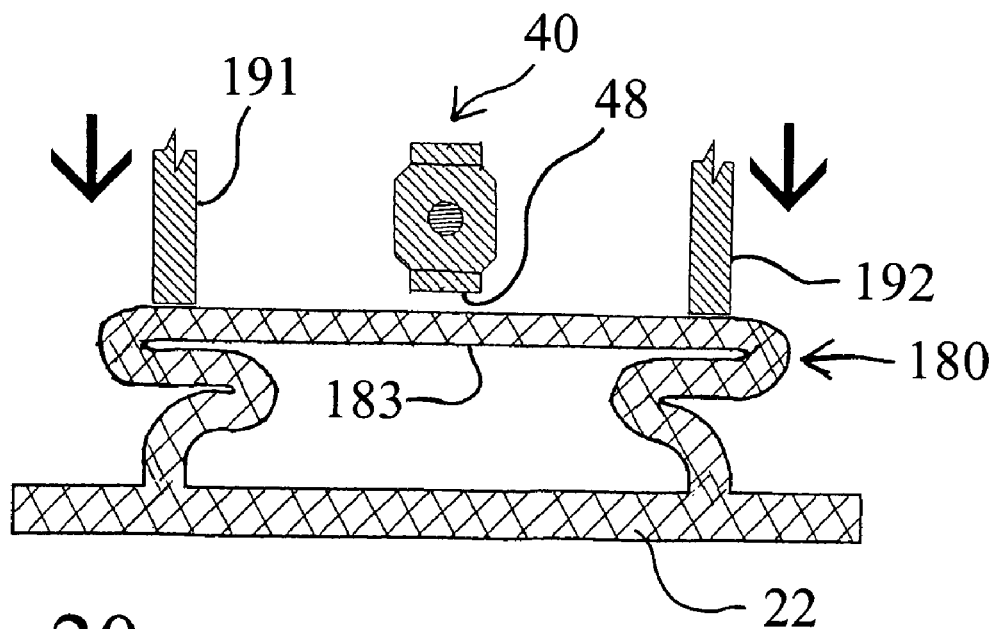
FIG. 20 is a schematic representation of the compressible trigger bar illustrated in FIG. 19 after it has been compressed by depression of the trigger.

FIG. 20 illustrates trigger bar 180 in its second deformed or compressed position wherein it is sufficiently compressed by blade arms 191 and 192 so that the device is fired. Abutment 48 no longer contacts the upper rail 183 of trigger bar 180 and the needle assembly is driven to its striking position by the mainspring. In the position shown in FIG. 20, trigger bar 180 is plastically deformed, i.e., it remains essentially in the position illustrated in FIG. 20 even if the blade arms 191 and 192 are lifted upwardly. In this fashion, the plastic deformation of arms 181 and 182 beyond their elastic limit prevents the trigger bar 180 from being able to return to its position where it is capable of holding or detaining the needle carrier assembly 40 in a cocked position.

Figure 21:
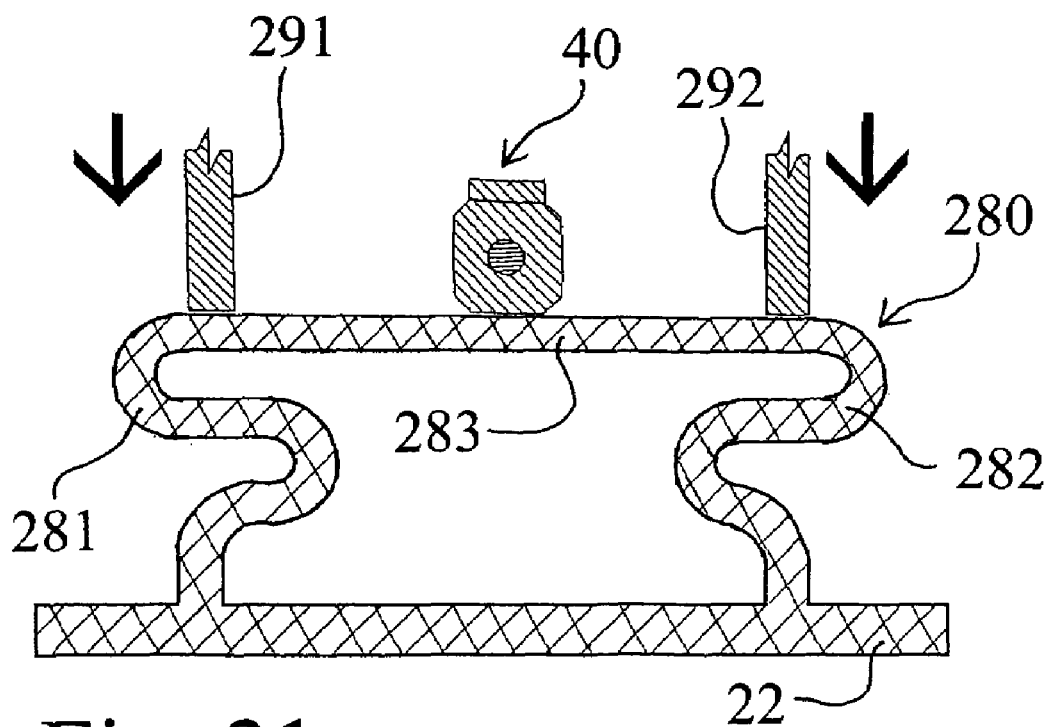
FIG. 21 is another alternate trigger bar, which is designed to be broken when compressed.
Figure 22:
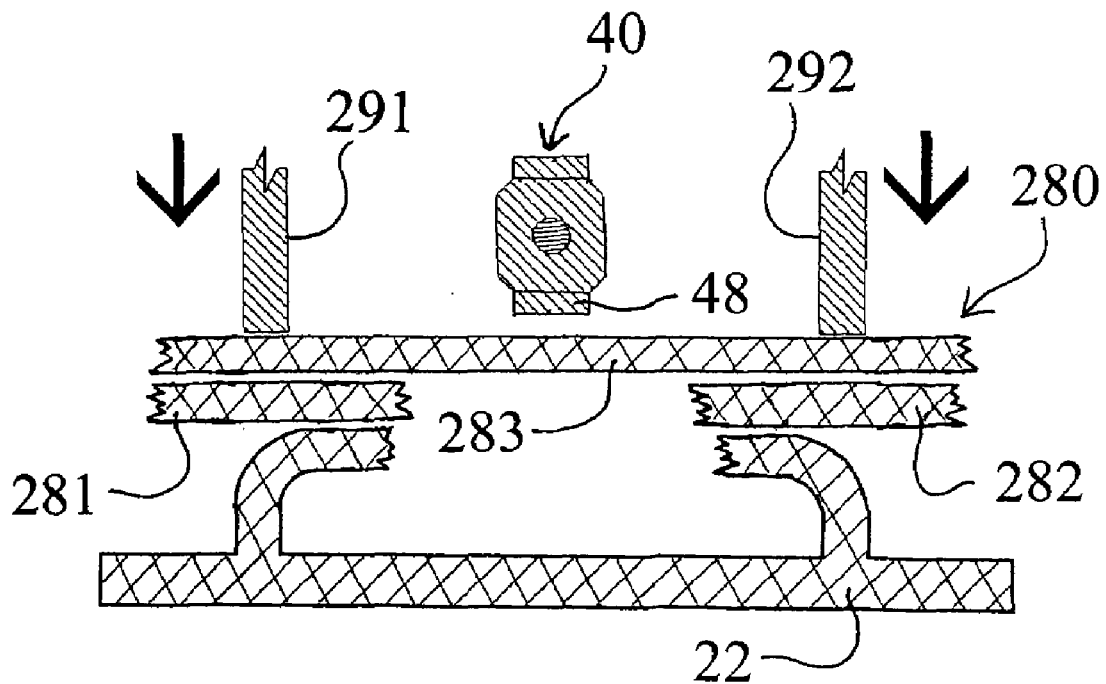
FIG. 22 is a schematic representation of the trigger bar illustrated in FIG. 21 after it has been deformed and broken, thereby releasing the needle assembly.

FIGS. 21 and 22 illustrate another trigger bar 280 having essentially the same design as that illustrated in FIG. 19, wherein generally S-shaped arms 281 and 282 and top rail 283 are integrally molded to lower body portion 22. Upper rail 283 holds abutment 48 (not visible in FIG. 21), thereby holding the needle carrier assembly 40 in its cocked position. Trigger bar 280 may be made of slightly more brittle plastic material than that illustrated in FIG. 19 and/or may be dimensioned in such a way to cause arms 281 and 282 to irreparably break as they are compressed by blade arms 291 and 292.

FIG. 22 illustrates the deformation of trigger bar 280 to the point where arms 282 and 281 have been irreparably broken with respect to top rail 283 and with respect to lower body 22. Breaking arms 281 and 282 renders them incapable of holding the needle assembly 40 in its cocked position, thereby limiting the device to a single use.

Figure 23:
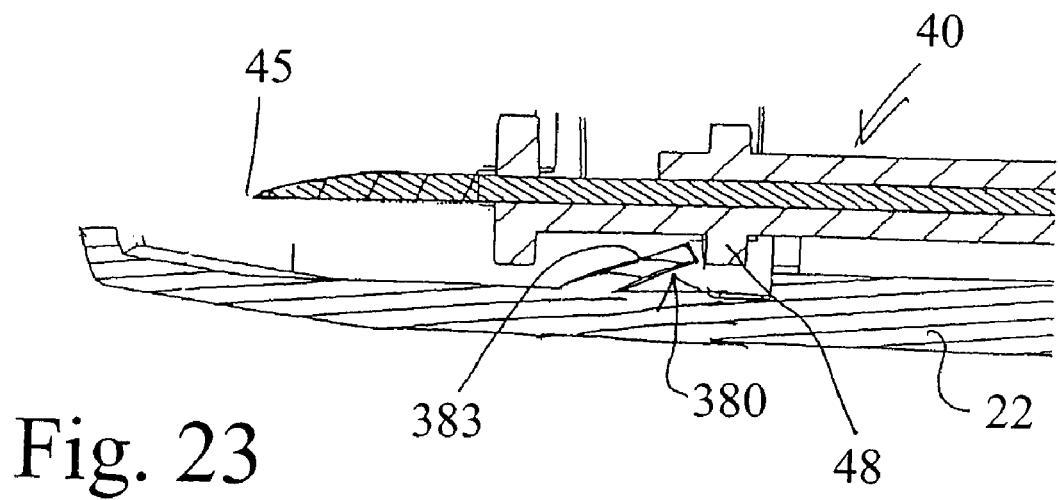
FIG. 23 is a side elevational view of an alternate breakable trigger bar.
Figure 24:
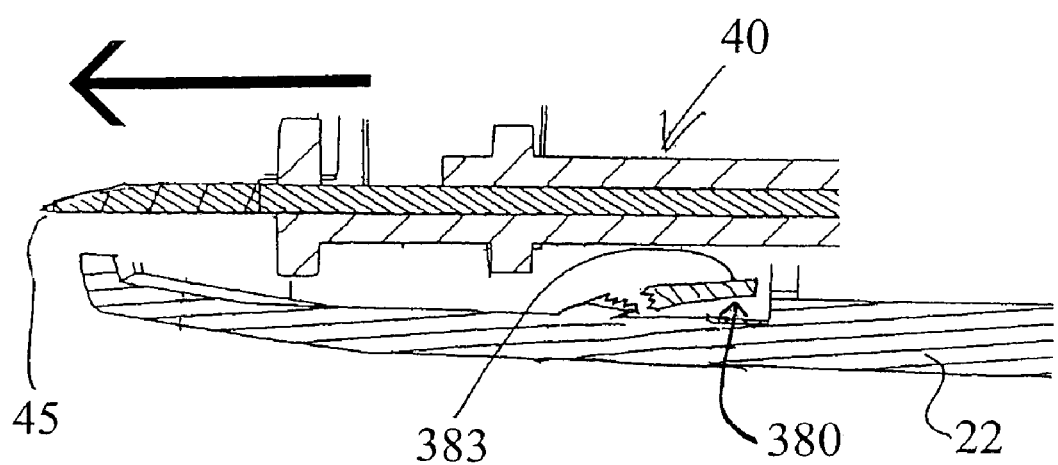
FIG. 24 is a schematic representation of the trigger bar shown in FIG. 23 after it has been deformed and broken, allowing the needle assembly to be driven to its striking position.

FIGS. 23 and 24 illustrate yet another break-away trigger bar 380. Trigger bar 380 is an inclined, rearwardly extending projection 383 molded as part of body portion 22 and bears against abutment 48 and holds needle carrier assembly 40 in its cocked position illustrated in FIG. 23.

FIG. 24 illustrates the second position of trigger bar 380 after the trigger of the device (not shown for clarity) has been depressed driving projection 383 downwardly as shown in FIG. 24 and causing it to break away from lower body portion 22. In its break-away position illustrated in FIG. 24, needle carrier assembly 40 is no longer held in its cocked position by trigger bar 383 and is driven to its striking position as shown by the arrow in FIG. 24.

The embodiments illustrated in FIGS. 19-24 are not as desirable as the partially severable trigger bar 83 shown best in FIGS. 17 and 18. Compressing or breaking a trigger bar is not as reliable as partially severing it, in large part because of the limited downward travel available to the trigger button.

Alternate blade designs may also be utilized. A single blade may be utilized, but the disadvantage in most single blade designs is asymmetrical or unbalanced loads. The double blade design of the preferred embodiment applies symmetrical loads. The blade or blades may also be designed to irreparably break the trigger bar as opposed to severing it, however, such designs may well require greater force to fire the device, and are therefore less desirable.

The foregoing description of the invention has been presented for purposes of illustration and description and is not intended to be exhaustive or to limit the invention to the precise form disclosed. Modifications and variations are possible in light of the above teaching. The embodiments were chosen and described to best explain the principles of the invention and its practical application to thereby enable others skilled in the art to best use the invention in various embodiments and with various modifications suited to the particular use contemplated. The scope of the invention is to be defined by the following claims.

What is claimed is:

1. A single-use disposable lancet device comprising:
    a body having an upper portion and a lower portion,
    a trigger carried by said upper portion of said body, said trigger movable between a first raised position wherein the device is cocked and a second depressed position wherein the device is fired,
    a needle assembly movable between a cocked position and a striking position,
    a drive spring for moving said needle assembly from its cocked position to its striking position,
    trigger bar means having a first position wherein said trigger bar means holds said needle assembly in its cocked position and having a second position wherein said needle assembly is moved to its striking position by said drive spring, wherein said trigger bar means is integrally molded as a part of said lower body portion,
    blade means carried by said trigger, and as said trigger moves from its first position to its second position, said blade means deforms a portion of said trigger bar means whereby said deformed trigger bar means releases said needle assembly from its cocked position and said deformed trigger bar means is thereafter not capable of holding said needle assembly in its cocked position, thereby limiting the device to a single use.

2. The device of claim 1 wherein said trigger bar means includes a transverse crossbar, said transverse crossbar having first and second ends, said first and second ends being severed by said blade means when said trigger is moved to said second position.

3. The device of claim 2 wherein said blade means comprises first and second guillotine type blades which sever said first and second ends of said transverse crossbar when the device is fired.

4. The device of claim 1 wherein said drive spring comprises a free floating spring and further comprising bounceback spring means integrally formed with said needle assembly.

5. The device of claim 4 wherein said bounceback spring means comprises a pair of spring arms.

6. The device of claim 5 wherein each of said spring arms is generally V-shaped.

7. The device of claim 1 wherein said trigger bar means is compressible by said blade means, and said trigger bar means has a first extended position in which the device is cocked and a second compressed position in which the device is fired.

8. The device of claim 1 wherein said trigger comprises:
a one-way trigger button molded into said upper portion of said body, said trigger button having a first raised and cocked position and a second depressed and firing position, said trigger button having distal and proximal ends pivotally connected to said body, said trigger button having a running length that exceeds the distance between said proximal and distal ends, so that said trigger button is stable only in its first and second positions and is unstable at any intermediate position.

9. A single-use disposable lancet device comprising:
a body having an upper portion and a lower portion,
a trigger carried by said upper portion of said body, said trigger movable between a first raised position in which the device is cocked and a second depressed position in which the device is fired,
a needle assembly movable between a cocked position and a striking position,
a drive spring for moving said needle assembly from its cocked position to its striking position,
trigger bar means having a first position wherein said trigger bar means holds said needle assembly in its cocked position and having a second position wherein said needle assembly is movable to its striking position by said drive spring, wherein said trigger bar means is integrally molded as a part of said lower body portion,
blade means carried by said trigger, and as said trigger moves from its first position to its second position, said blade means severs a portion of said trigger bar means causing said partially severed trigger bar means to release said needle assembly from its cocked position and thereafter preventing said partially severed trigger bar means from holding said needle assembly in its cocked position, thereby limiting the device to a single use.

10. The device of claim 9 wherein said trigger bar means includes a transverse crossbar, said transverse crossbar having first and second ends, said first and second ends being severed by said blade means when said trigger is moved to said second position.

11. The device of claim 10 wherein said blade means comprises first and second guillotine type blades which sever said first and second ends of said transverse crossbar when the device is fired.

12. The device of claim 11 wherein said trigger bar means includes a support stem to prevent said transverse crossbar from falling out of said body after said first and second ends are severed.

13. The device of claim 9 wherein said drive spring comprises a free floating spring and further comprising bounceback spring means integrally formed with said needle assembly.

14. The device of claim 13 wherein said bounceback spring comprises a pair of generally V-shaped spring arms.

15. The device of claim 9 wherein said trigger comprises:
a one-way trigger button molded into said upper portion of said body, said trigger button having a first retracted and cocked position and a second depressed and firing position, said trigger button having distal and proximal ends pivotally connected to said upper portion of said body, said trigger button having a running length that exceeds the distance between said proximal and distal ends, so that said trigger button is stable only in its first and second positions and is unstable at any intermediate position.

16. A single-use disposable lancet device comprising:
a body having an upper portion and a lower portion,
a trigger carried by said upper portion of said body, said trigger movable between a first raised position in which the device is cocked and a second depressed position in which the device is fired,
a needle assembly movable between a cocked position and a striking position,
a free-floating drive spring for moving said needle assembly from its cocked position to its striking position,
a bounceback spring means integrally formed with said needle assembly,
trigger bar means having a first position wherein said trigger bar means holds said needle assembly in its cocked position and having a second position wherein said needle assembly is moved to its striking position by said drive spring,
blade means carried by said trigger, and as said trigger moves from its first position to its second position, said blade means severs a portion of said trigger bar means whereby said partially severed trigger bar means releases said needle assembly from its cocked position and said partially severed trigger bar means is thereafter not capable of holding said needle assembly in its cocked position, thereby limiting the device to a single use.

17. The device of claim 16 wherein said trigger bar means includes a support stem and a transverse crossbar, said transverse crossbar having first and second ends, said first and second ends being severed by said blade means when said trigger is moved to said second position.

18. The device of claim 17 wherein said blade means comprises first and second guillotine-type blades which sever said first and second ends of said transverse crossbar when the device is fired.

19. The device of claim 16 wherein said trigger comprises:
a one-way trigger button molded into said upper portion of said body, said trigger button having a first retracted and cocked position and a second depressed and firing position, said trigger button having distal and proximal ends pivotally connected to said upper portion of said body, said trigger button having a running length that exceeds the distance between said proximal and distal ends, so that said trigger button is stable only in its first and second positions and is unstable at any intermediate position.

20. A single-use disposable lancet device comprising:
a body having an upper portion and a lower portion,
a trigger carried by said upper portion of said body, said trigger movable between a first raised position in which the device is cocked and a second depressed position in which the device is fired,
a needle assembly movable between a cocked position and a striking position,
a drive spring for moving said needle assembly from its cocked position to its striking position,
trigger bar means having a first position wherein said trigger bar means holds said needle assembly in its cocked position and having a second position wherein said needle assembly is moved to its striking position by said drive spring, wherein said trigger bar means is integrally molded as part of said lower body portion,
blade means carried by said trigger, and as said trigger moves from its first position to its second position, said blade means irreparably breaks a portion of said trigger bar means whereby said broken trigger bar means releases said needle assembly from its cocked position and said broken trigger bar means is thereafter not capable of holding said needle assembly in its cocked position, thereby limiting the device to a single use.

21. The apparatus of claim 20 further comprising a depressible trigger button, wherein the depressible trigger button carries two vertical blades which sever a portion of said trigger bar means when the trigger button is depressed.

22. The apparatus of claim 20 in which a support stem is molded onto the trigger bar and is bendable downward when the device is fired, thereby retaining the trigger bar within the body of the device.

23. In a lancet device for drawing a capillary blood sample, wherein a needle assembly is carried within a body, and said needle assembly is movable between a cocked position, a striking position and an at rest position, the improvement comprising:
a free floating mainspring means for driving said needle assembly from its cocked position to its striking position, and
bounceback spring means carried by said needle assembly for returning said needle assembly from said striking position to said at rest position, said bounceback spring means being integrally formed with said needle assembly, wherein said bounceback spring means comprises a pair of spring arms.

24. The device of claim 23 wherein each of said spring arms is generally V-shaped.

25. The method of automatically assembling a lancet device in a cocked position, wherein the components of said lancet device include an upper body portion having proximal and distal ends, a lower body portion having proximal and distal ends, a mainspring and a needle assembly having a removable tailpiece, and wherein an opening is formed in said proximal ends of one or both of said body portions of said device for temporarily receiving said tailpiece, comprising the steps:
supporting said lower body portion,
automatically loading said mainspring onto said tailpiece,
automatically compressing said mainspring on said tailpiece,
automatically and temporarily holding said compressed mainspring on said tailpiece,
automatically loading said needle assembly with said compressed mainspring into said lower body portion,
automatically closing the device by attaching said upper body portion to said lower body portion, and
severing said tailpiece from said needle assembly, leaving said cocked mainspring in position ready to cause said needle assembly to fire.

26. The method of claim 25 wherein said mainspring is compressed and held on said tailpiece by an automatic compression tool, and wherein said automatic compression tool is withdrawn through said opening after the device is closed.

27. The method of assembling a lancet device in a cocked position, wherein the components of said lancet device include an upper body portion having proximal and distal ends, a lower body portion having proximal and distal ends, a mainspring and a needle assembly having a removable tailpiece, and wherein an opening is formed in said proximal ends of one or both of said body portions of said device for temporarily receiving said tailpiece, comprising the steps:
supporting said lower body portion,
loading said mainspring onto said tailpiece,
compressing said mainspring on said tailpiece,
temporarily holding said compressed mainspring on said tailpiece,
loading said needle assembly with said compressed mainspring into said lower body portion,
closing the device by attaching said upper body portion to said lower body portion, and
severing said tailpiece from said needle assembly, leaving said cocked mainspring in position ready to cause said needle assembly to fire.

28. The method of claim 27 wherein said mainspring is compressed and held on said tailpiece by a compression tool, and wherein said compression tool is withdrawn through said opening after the device is closed.

29. In a single-use disposable lancet device having a body with upper and lower portions, a needle assembly movable between a cocked position and a striking position, and a drive spring for advancing said needle assembly, the improvement comprising:
a one-way trigger button molded into said upper portion of said body, said trigger button having a first retracted and cocked position and a second depressed and firing position, said trigger button having distal and proximal ends pivotally connected to said body, said trigger button having a running length that exceeds the distance between said proximal and distal ends, so that said trigger button is stable only in its first and second positions and is unstable at any intermediate position.

30. The device of claim 29 wherein said trigger button comprises three segments, a first segment forming said distal end of said trigger button which is concave and adapted to comfortably receive a user's fingertip, a second segment forming said proximal end of said trigger button, and a third segment which is positioned between said first and second segments.

31. The device of claim 30 wherein said third segment is inclined between said first and second segments.

32. The device of claim 31 wherein said three segments create an over-the-center motion of said trigger, wherein said trigger is unstable at intermediate positions between said cocked and firing positions.

33. The device of claim 32, wherein said trigger button remains in its depressed firing position after the device is fired.

* * * * *